US012734330B2

(12) United States Patent
Abitabilo et al.

(10) Patent No.: US 12,734,330 B2
(45) Date of Patent: Sep. 15, 2026

(54) CLOSED SYSTEM CATHETER

(71) Applicant: Smiths Medical ASD, Inc., Plymouth, MN (US)

(72) Inventors: James Edward Abitabilo, Bristol, CT (US); Gursel Akcay, Madison, CT (US); Jay T. Breindel, Branford, CT (US); Harsh D. Chheda, Cheshire, CT (US); Kathryn Felicito, Cheshire, CT (US); David J. Goral, Brookfield, CT (US); James Muskatello, Southington, CT (US); Christopher Roehl, New Hartford, CT (US)

(73) Assignee: ICU MEDICAL, INC., San Clemente, CA (US)

(*) Notice: Subject to any disclaimer, the term of this patent is extended or adjusted under 35 U.S.C. 154(b) by 153 days.

(21) Appl. No.: 18/202,181

(22) Filed: May 25, 2023

(65) Prior Publication Data

US 2023/0310801 A1 Oct. 5, 2023

Related U.S. Application Data

(62) Division of application No. 16/894,334, filed on Jun. 5, 2020, now Pat. No. 12,343,482, which is a division (Continued)

(51) Int. Cl.
*A61M 25/00* (2006.01)
*A61M 25/01* (2006.01)
(Continued)

(52) U.S. Cl.
CPC .... *A61M 25/0097* (2013.01); *A61M 25/0108* (2013.01); *A61M 25/0606* (2013.01); (Continued)

(58) Field of Classification Search
CPC .......... A61M 25/0097; A61M 25/0108; A61M 25/0606; A61M 25/0612; A61M 25/0618; (Continued)

(56) References Cited

U.S. PATENT DOCUMENTS 5,032,116 A * 7/1991 Peterson ........... A61M 25/0693 604/168.01
8,647,310 B2 2/2014 Fangrow, Jr. et al.
(Continued)

FOREIGN PATENT DOCUMENTS

EP 0820319 B1 2/2003
WO 2015123689 A1 8/2015

OTHER PUBLICATIONS

EP Search Report for EP 23214060.8 dated Mar. 18, 2024.
AU Examination Report dated Jun. 12, 2024 for AU patent application No. 2023203163.

*Primary Examiner* — Kevin C Sirmons
*Assistant Examiner* — Antarius S Daniel
(74) *Attorney, Agent, or Firm* — Louis Woo

(57) ABSTRACT

A catheter hub assembly. The catheter hub assembly includes a catheter hub body, a septum and a septum retainer, the catheter hub body having a distal end, a proximal and an internal wall defining an internal fluid passageway therebetween, the internal wall defining a transitional step within the internal fluid passageway, the septum positioned within the internal fluid passageway such that a distal end of the septum abuts up against the transitional step, the septum retainer at least partially receivable within the internal fluid passageway and having an outer wall shaped and sized to interlock with the inner wall of the catheter hub body, the outer wall including one or more lateral ribs configured to inhibit rotation of the septum retainer relative to the catheter hub body.

19 Claims, 30 Drawing Sheets

Related U.S. Application Data of application No. 15/435,700, filed on Feb. 17, 2017, now Pat. No. 10,675,440.

(60) Provisional application No. 62/413,784, filed on Oct. 27, 2016, provisional application No. 62/351,040, filed on Jun. 16, 2016, provisional application No. 62/296,865, filed on Feb. 18, 2016.

(51) Int. Cl.

| | |
|---|---|
| ***A61M 25/06*** | (2006.01) |
| ***A61M 39/06*** | (2006.01) |
| ***A61M 39/10*** | (2006.01) |
| ***A61M 39/28*** | (2006.01) |

(52) U.S. Cl.

CPC .... *A61M 25/0625* (2013.01); *A61M 25/0631* (2013.01); *A61M 25/0637* (2013.01); *A61M 25/0693* (2013.01); *A61M 39/0606* (2013.01); *A61M 39/10* (2013.01); *A61M 39/28* (2013.01); *A61M 2039/062* (2013.01); *A61M 2039/0626* (2013.01); *A61M 2039/0633* (2013.01); *A61M 2039/064* (2013.01); *A61M 2039/0653* (2013.01); *A61M 2039/0686* (2013.01); *A61M 2039/1072* (2013.01); *A61M 2205/581* (2013.01); *A61M 2205/582* (2013.01)

(58) Field of Classification Search

CPC .. A61M 25/0631; A61M 39/10; A61M 39/20; A61M 39/28; A61M 39/062; A61M 39/1072; A61M 2039/205; A61M 25/0693

See application file for complete search history.

(56) References Cited

U.S. PATENT DOCUMENTS

| | | | | |
|---|---|---|---|---|
| 10,195,415 | B2 * | 2/2019 | Yeh ...................... | A61M 39/26 |
| 2004/0127854 | A1 | 7/2004 | Leinsing et al. | |
| 2005/0043709 | A1 * | 2/2005 | Brimhall ........... | A61M 25/0637 604/512 |
| 2007/0156118 | A1 * | 7/2007 | Ramsey ................ | A61M 39/20 604/533 |
| 2014/0249476 | A1 | 9/2014 | Grimm et al. | |
| 2014/0276215 | A1 | 9/2014 | Nelson et al. | |
| 2017/0120016 | A1 * | 5/2017 | Burkholz .......... | A61M 25/0693 |

* cited by examiner 103
104
105
106
262
264
266
268
270
272
274
276
278
280
282
284
286
288
290
292

Section AA

Section AA

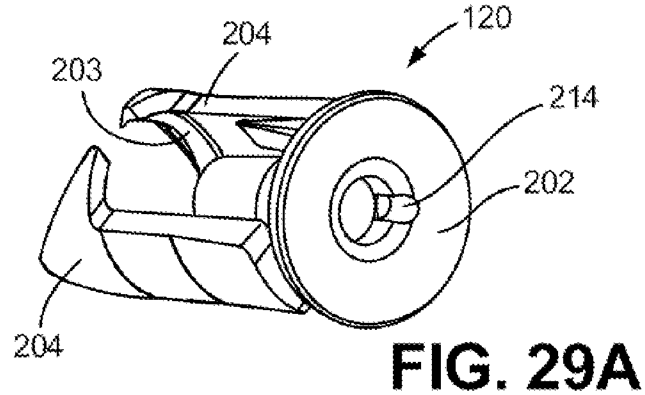
FIG. 29A
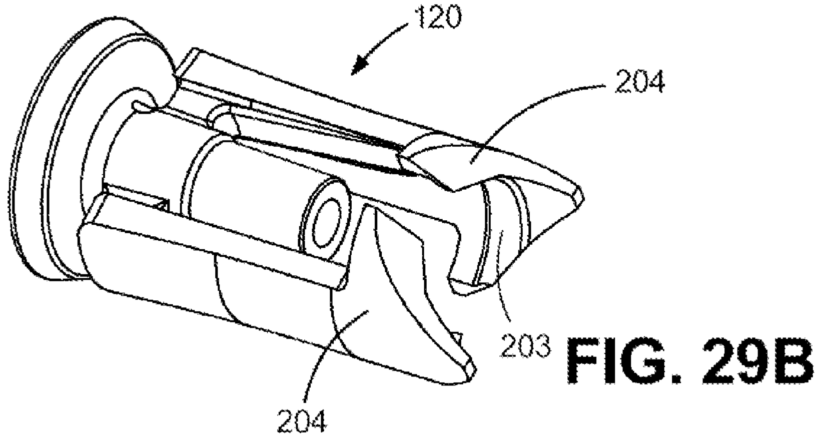
FIG. 29B
FIG. 29C
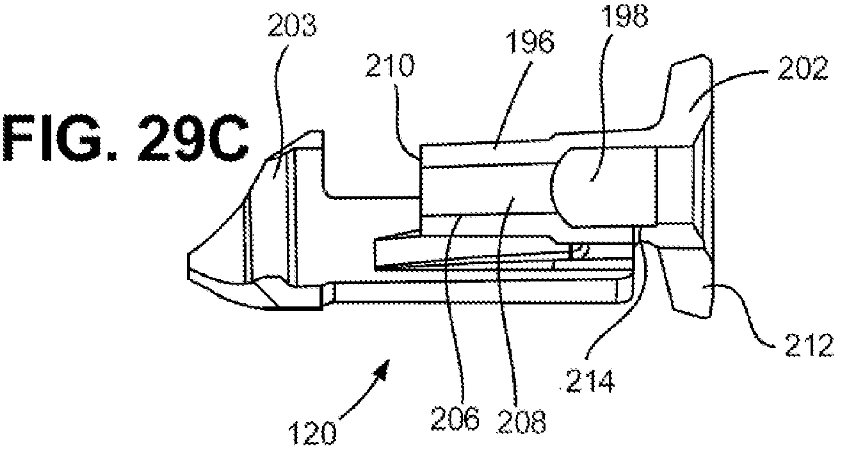

CLOSED SYSTEM CATHETER

RELATED APPLICATIONS

This application is a division of application Ser. No. 16/894,334 filed Jun. 5, 2020, which claims priority from application Ser. No. 15/435,700 filed Feb. 17, 2017, now U.S. Pat. No. 10,675,445, which in turn claims the benefit of U.S. Provisional Application Nos. 62/296,865 filed Feb. 18, 2016; 62/351,040 filed. Jun. 16, 2016; 62/367,748 filed Jul. 28, 2016; and 62/413,784 filed Oct. 27, 2016, each of which are fully incorporated herein by reference.

TECHNICAL FIELD

The present disclosure relates generally to intravenous catheters, and more particularly to closed system intravenous catheter assemblies having an improved catheter hub design.

BACKGROUND

Intravenous (IV) therapy is a versatile technique used for the administration of medical fluids to and withdrawal of bodily fluids from patients. IV therapy has been used for various purposes such as the maintenance of fluid and electrolyte balance, the transfusion of blood, the administration of nutritional supplements, chemotherapy, and the administration of drugs and medications. These fluids, collectively referred to herein as medicaments, may be administered intravenously by injection through a hypodermic needle, or intermittently or continuously by infusion using a needle or catheter. A common intravenous access device utilized by clinicians is the peripheral IV catheter.

A peripheral IV catheter is made of soft, flexible plastic or silicone, generally between fourteen to twenty-four gauge in size. In the conventional venipuncture procedure, a catheter is inserted into a vein in the patient's hand, foot, or the inner aspect of the arm or any vein in the body that will accept an IV catheter. In order to place the IV catheter into a patient's vein, a sharp introducer needle is used to puncture the skin, tissue, and vein wall to provide a path for placement of the catheter into the vein.

Referring to FIGS. 1A-B, a conventional IV needle assembly 50 configured for insertion of an "over the needle" catheter 52 is depicted. Catheter 52 generally includes a catheter tube 54 having a distal end 56 for insertion into a biological site, a proximal end 58 and a flexible wall defining a lumen extending therebetween. Frequently, the proximal end 58 of the catheter tube 54 is operably coupled to a catheter hub 60. Catheter 52 can be operably coupleable to the needle assembly 50, in part by positioning the catheter 52 coaxially over a needle 62 of the needle assembly 50. The catheter 52 thus rides with the needle 62 through the skin, tissue and vein wall and into the patient's vein. Once the catheter tube 54 has been entered into the patient's vein, the catheter 52 can be advanced further into the vein as desired and the needle 62 can be withdrawn from the catheter 52. The catheter 52 can then be secured into place on the patient and connected to an IV fluid supply. In some instances, catheter 52 can include an extension tube 64 having a clamp 66 and a Luer lock connector 68 for connection to an IV fluid supply. Such catheters are often referred to as closed system catheters, as typically they include a septum that seals the needle path after the needle 62 has been withdrawn from the catheter 52, thereby preventing blood or bodily fluid from the patient from escaping from the catheter to the ambient environment.

SUMMARY OF THE DISCLOSURE

Embodiments of the present disclosure provide a simple and reliable method of constructing a catheter hub in which the various components of the catheter hub are snap fit together, such that adhesives and ultrasonic welding are not required, thereby reducing the expense and labor required during construction of a catheter assembly. Some embodiments of the present disclosure further provide a mechanism for inhibiting rotation of the various components within the catheter hub, as well as inhibiting rotation of the catheter hub relative to a needle insertion device. Some embodiments of the present disclosure provide a catheter hub having an improved wing design configured to improve contact with a patient's skin when a portion of the catheter assembly is inserted into a vein of the patient.

One embodiment of the present disclosure provides a catheter hub assembly including a catheter hub body, a septum and a septum retainer. The catheter hub body can have a distal end operably coupled to a catheter tube, a proximal end, and an internal wall defining an internal fluid passageway therebetween. The internal wall can define a transitional step within the internal fluid passageway between a smaller diameter portion proximal to the distal end, and a larger diameter portion proximal to the proximal end. The septum can have a distal end and a proximal end. The septum can be positioned within the internal fluid passageway such that the distal end of the septum abuts up against the transitional step. The septum retainer can be at least partially receivable within the internal fluid passageway of the catheter hub body. The septum retainer can have an outer wall and an inner wall. The outer wall of the septum retainer can be shaped and sized to interlock with the inner wall of the catheter hub body and can include one or more lateral ribs configured to inhibit rotation of the septum retainer relative to the catheter hub body.

One embodiment of the present disclosure further provides a catheter insertion device having a needle assembly and a needle housing. The needle assembly can include an insertion needle presenting a sharpened needle tip. The insertion needle can be operably coupled to the needle housing and can be shiftable between a ready for use position in which the sharp needle tip of the insertion needle extends from the needle housing, and a safe position in which the sharpened needle tip of the insertion needle is housed within the needle housing.

In one embodiment, the proximal end of the catheter hub body includes a lug configured to align a catheter hub relative to the catheter insertion device and aid in coupling of the catheter hub assembly to a passive release mechanism of the catheter insertion device. In one embodiment, the septum is configured to seal the internal fluid passageway upon removal of the needle from the needle insertion device passing therethrough. In one embodiment, the septum includes an internal surface defining an aperture. In one embodiment, the septum is circumferentially compressed by the internal wall of the catheter hub to aid in resealing of the septum upon removal of the needle.

In one embodiment, the internal wall of the catheter hub body further defines a side port. In one embodiment, the catheter assembly further includes extension tubing operably coupled to the side port, wherein a lumen of the extension tube is in fluid communication with the internal fluid passageway. In one embodiment, the catheter assembly further includes an extension tube clamp operably coupled to the extension tube and configured to selectively occlude the extension tube to inhibit flow through the extension tube lumen.

In one embodiment, the catheter assembly further includes a needleless connector operably coupled to and in fluid communication with a lumen of the extension tube. In one embodiment, the needleless connector is shiftable between an actively open position and a biased close position. In one embodiment, the catheter assembly further includes a vent cap operably coupled to the needleless connector. In one embodiment, the vent cap is configured to shift between a first, storage position in which the needleless connector remains closed, and a second, actively depressed position in which the needleless connector is opened, thereby venting air trapped within the catheter assembly.

Another embodiment of the present disclosure provides a catheter hub assembly including a catheter hub body, a septum and a septum retainer. The catheter hub body can have a distal end operably coupled to a catheter tube, a proximal end, and an internal wall defining an internal fluid passageway therebetween. The internal wall can define a transitional step within the internal fluid passageway between a smaller diameter portion proximal to the distal end and a larger diameter portion proximal to the proximal end. The septum can have a distal end and a proximal end. The septum can be positioned within the internal fluid passageway such that the distal end of the septum abuts up against the transitional step. The septum retainer can be at least partially receivable within the internal fluid passageway of the catheter hub body, and can be configured to secure the septum in position within the internal fluid passageway. The septum retainer can have an outer wall and an inner wall. The outer wall can be shaped and sized to interlock with the inner wall of the catheter hub body and can include one or more lateral ribs configured to inhibit rotation of the septum retainer relative to the catheter hub body. The inner wall can be shaped and sized to selectively couple the catheter hub assembly to a catheter insertion device, and can include one or more lateral nubs configured to inhibit rotation of the septum retainer relative to the catheter insertion device. In one embodiment, a frictional resistance provided by the one or more lateral ribs can exceed a frictional resistance provided by the one or more lateral nubs, such that the septum retainer is configured to rotate relative to the catheter insertion device before rotating relative to the catheter hub body.

One embodiment of the present disclosure further provides a closed system catheter assembly including a catheter insertion device. The catheter insertion device can include a needle assembly and a needle housing. The needle assembly can include an insertion needle presenting a sharpened needle tip. The insertion needle can be operably coupled to the needle housing and shiftable between a ready for use position in which the sharpened needle tip of the insertion needle extends from the needle housing, and a safe position in which the sharpened needle tip of the insertion needle is housed within the needle housing.

In one embodiment, the proximal end of the catheter hub body can include a lug configured to align the catheter hub relative to the catheter insertion device and aid in coupling the catheter hub assembly to a passive release mechanism of the catheter insertion device. In one embodiment, the septum can be configured to seal the internal fluid passageway upon removal the insertion needle of the catheter insertion device passing therethrough. In one embodiment, the septum can include an internal surface defining an aperture. In one embodiment, the septum can be circumferentially compressed by the internal wall of the catheter hub to aid in resealing of the septum upon removal of the insertion needle.

In one embodiment, the internal wall of the catheter hub body can define a side port. In one embodiment, an extension tube can be operably coupled to the side port, Therein a lumen of the extension tube is in fluid communication with the internal fluid passageway. In one embodiment, an extension tube clamp can be operably coupled to the extension tube and can be configured to selectively occlude the extension tube to inhibit flow through the extension tube lumen. In one embodiment, a needleless connector can be operably coupled to and in fluid communication with the lumen of the extension tube. In one embodiment, the needleless connector can be shiftable between an actively open position and a biased closed position. In one embodiment, the catheter hub assembly can further include a vent cap operably coupled to the needleless connector. In one embodiment, the vent cap can be configured to shift between a first, storage position in which the needleless connector remains closed, and a second, actively depressed position in which the needleless connector is opened, thereby venting air trapped within the catheter hub assembly.

Another embodiment of the present disclosure provides a catheter assembly configured for insertion into a subject's vein, including a catheter hub and a wing assembly. The catheter hub can have a distal end operably coupled to a catheter tube and a proximal end configured to be operably coupled to a catheter insertion device. The wing assembly can be operably coupled to the catheter hub and can include a pair of flexible wings, a heel portion and a collar. The pair of flexible wings can extend outwardly from a central axis of the catheter hub. The heel portion can extend from a proximal end of the pair of flexible wings towards the proximalend of the catheter hub. The collar can wrap around a central axis of the catheter hub. The bottom surface of the pair of wings and a bottom surface of the heel portion can form a contiguous surface that is angled relative to an axis of the catheter tube such that the catheter tube is substantially straight when inserted into vein of the subject and the contiguous surface is substantially parallel to the skin of the subject.

One embodiment of the present disclosure further provides a closed system catheter assembly including a catheter insertion device. The catheter insertion device can include a needle assembly and a needle housing. The needle assembly can include an insertion needle presenting a sharpened needle tip. The insertion needle can be operably coupled to the needle housing and shiftable between a ready for use position in which the sharpened needle tip of the insertion needle extends from the needle housing, and a safe position in which the sharpened needle tip of the insertion needle is housed within the needle housing.

In one embodiment, the contiguous surface can be offset from the axis of the catheter tube by a range of between seven and nine degrees. In one embodiment, the contiguous surface can be offset from the axis of the catheter tube by approximately eight degrees. In one embodiment, a distal portion of the pair of wings can form a substantially straight line extending substantially orthogonal to the axis of the catheter tube for improved contact with the skin of the subject. In another embodiment, a distal portion of the pair of wings can be concave, so as to form a slight arc, such that the distal edge of the wings extends distally farther than the distal portion of the pair of wings proximal to the catheter tube. In one embodiment, a top surface of the pair of wings can define a concave surface configured to aid a clinician and gripping the catheter assembly. In one embodiment, the wing assembly can have a lower modulus of elasticity than the catheter hub. In one embodiment, a textured pattern can be formed into the contiguous surface to increase the frictional resistance with the skin of the subject when the catheter tube is inserted into vein of the subject. In one embodiment, the textured pattern can aid in preventing perspiration build up, which can occur with a flat or smooth surface. In one embodiment, the textured pattern inhibits the creation of high-pressure areas that may cause discomfort. In one embodiment, the wing assembly is integrally molded onto the catheter hub. In one embodiment, the collar at least partially wraps around the proximal portion of the catheter hub. In one embodiment, the catheter hub can include one or more ledges configured to provide a structural reinforcement for the pair of flexible wings.

Another embodiment of the present disclosure provides a vent cap configured to be operably coupled to a needleless connector and shiftable relative to the needleless connector between a storage position and an actively depressed, venting position. The vent cap can include a nose, a push plate and one or m ore resilient needleless connector engagement arms. The nose can be configured to be inserted at least partially into the needleless connector when the vent cap is pushed to the actively depressed, venting position. The push plate can be operably coupled to the proximal end of the nose and can define a vent aperture comprising an air permeable membrane. The one or more resilient needleless connector engagement arms can be operably coupled to the nose and can be configured to grip a portion of the needleless connector, wherein the one or more resilient needleless connector engagement arms bias the vent cap to the storage position.

In one embodiment, the vent cap is selectively coupled to a closed system catheter assembly, including a catheter tube, catheter hub, extension tube, and needleless connector. In one embodiment, the one or more resilient needleless connector engagement arms can include a ridge to improve a grip of the one or more resilient needleless connector engagement arms to the needleless connector. In one embodiment, shifting of the vent cap to the actively depressed, venting position enables air trapped within the needleless connector to be purged. In one embodiment, shifting the vent cap to the actively depressed, venting position forces the one or more resilient needleless connector engagement arms apart, and where upon release from the actively depressed position, the resiliency of the one or more resilient needleless connector engagement arms biases the vent cap back to the storage position. In one embodiment, the vent cap is removable from the needleless connector after use. In one embodiment, the nose of the vent cap is tapered to improve a fluid tight seal with the needleless connector when shifted to the actively depressed, venting position.

In one embodiment, the nose includes a vent path sealed at one end by the air permeable membrane. In one embodiment, the vent path is constructed of at least one of a transparent and translucent material. In one embodiment, the vent cap is configured to provide a flashback indication as fluid flows into the vent path. In one embodiment, the push plate can define an eyelet configured to provide a fluid path for air escaping from the vent path.

Another embodiment of the present disclosure provides an intravenous catheter assembly including a catheter insertion device and a closed system catheter. The catheter insertion device can include a needle assembly and a needle housing. The needle assembly can include an insertion needle presenting a sharpened needle tip. The insertion needle can be operably coupled to the needle housing and shiftable between a ready for use position in which the sharpened needle tip of the insertion needle extends from the needle housing, and a safe position in which the sharpened needle tip of the insertion needle is housed within the needle housing. The insertion needle can include structure presenting a notch position proximal to the sharpened needle tip of the insertion needle that is configured to enable blood to flow therethrough to provide a primary indication of catheter placement. The needle assembly can include structure defining a flash chamber in communication with a lumen of the insertion needle to provide a secondary indication of catheter placement.

The closed system catheter can include a catheter tube, a catheter hub, an extension tube, a needleless connector, and a vent cap. The vent cap can include a wall defining a vent path sealed at one end by an air permeable barrier. The vent cap can be shiftable between a first storage position in which the needleless connector is in a closed position, and a second actively depressed position in which the needleless connector is shifted to an open position, thereby venting air trapped within the closed system catheter and enabling blood to flow into the vent path to provide a tertiary indication of catheter placement.

A method of the present disclosure provides using an intravenous catheter assembly including a flash chamber and a vent cap including one or more of the following steps:

- introducing an insertion needle and catheter tube coaxially positioned there about into a vein of the subject, wherein an annular space is present between the insertion needle and the coaxially positioned catheter tube;
- receiving a primary indication of proper catheter placement via blood flow through a notch defined in the insertion needle into the annular space;
- receiving a secondary indication of proper catheter placement via blood flow through a lumen of the insertion needle and into the flash chamber;
- venting air from within the intravenous catheter assembly by shifting the vent cap from a storage position to an actively depressed position; and
- receiving a tertiary indication of proper catheter placement via blood flow into the vent cap.

The summary above is not intended to describe each illustrated embodiment or every implementation of the present disclosure. The figures and the detailed description that follow more particularly exemplify these embodiments.

BRIEF DESCRIPTION OF THE DRAWINGS

The disclosure can be more completely understood in consideration of the following detailed description of various embodiments of the disclosure, in connection with the accompanying drawings, in which:

FIG. 29A is a perspective view depicting a vent cap in accordance with an embodiment of the disclosure.

FIG. 29B is another perspective view depicting the vent cap of FIG. 29A.

FIG. 29C is a sectional view depicting the vent cap of FIG. 29A.

Figures 1A, 1B:
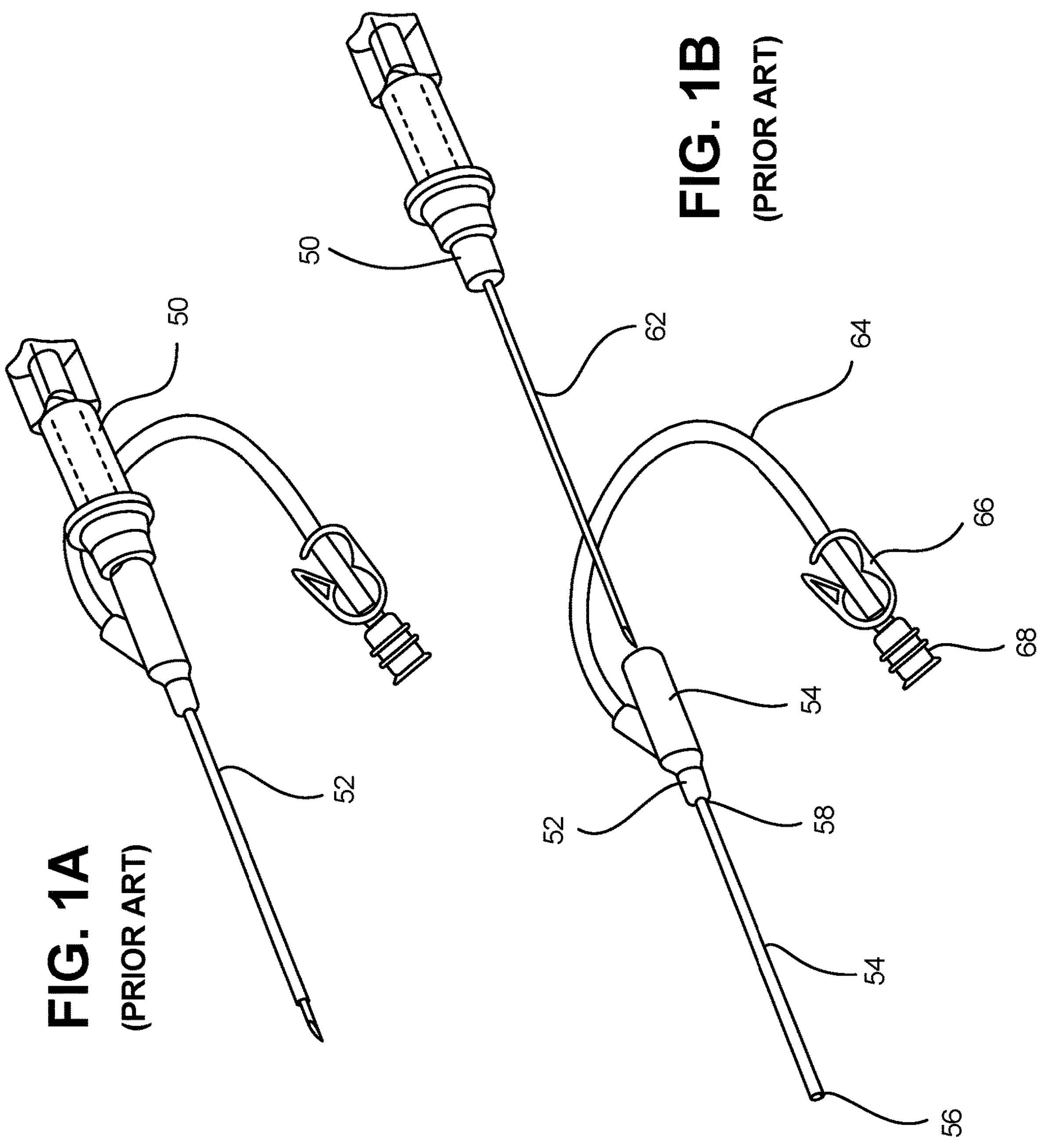
FIG. 1A is a perspective view depicting a conventional IV needle assembly with a catheter positioned over a needle.
FIG. 1B is a perspective view depicting the conventional IV needle assembly of FIG. 1A with the catheter removed from the needle.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the disclosure as defined by the appended claims.

DETAILED DESCRIPTION

Referring to FIGS. 1A-B, a conventional IV catheter assembly 20 is depicted. Details of the conventional IV catheter assembly 20 are described in the Background section above.

Referring to FIGS. 2A-G, a catheter assembly 100 is depicted in accordance with an embodiment of the disclosure. In one embodiment, the catheter assembly 100 can be a closed system catheter. Referring to FIGS. 3A-G, a closed system catheter assembly 101 is depicted in accordance with an embodiment of the disclosure. In one embodiment, the closed system catheter assembly 101 can include a catheter assembly 100 operably coupled to a catheter insertion device 102.

I. Catheter Insertion Device

Catheter insertion device 102 can provide an insertion needle 104, over which a portion of a catheter tube 108 coaxially rides. Various types of catheter insertion devices 102 are marketed by Smiths Medical ASD, Inc. of St. Paul, Minn., under the TELCO trademark. One embodiment of a catheter insertion device 102 (such as that depicted in FIGS. 1A-B) is described in U.S. Pat. Nos. 7,291,130 and 8,257,322 (depicting an IV catheter insertion device marketed by Smiths Medical ASD, Inc. under the INTUITIV trademark), both of which are incorporated by reference herein.

Figure 4A:
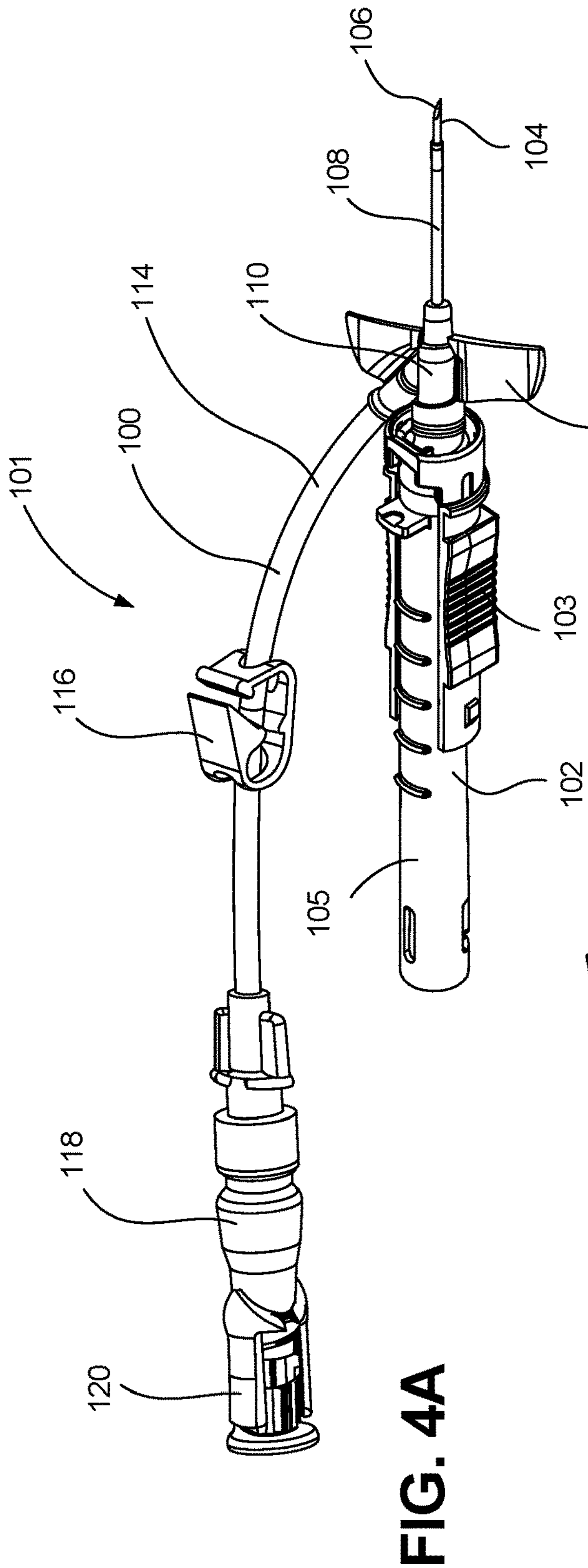
FIG. 4A is a perspective view depicting an intravenous catheter assembly having a catheter operably coupled to a catheter insertion device in accordance with an embodiment of the disclosure, wherein the catheter insertion device is in the ready for use position.

In other embodiments, the catheter insertion device 102 can provide a safety needle assembly (such as that depicted in FIGS. 3A-G and FIGS. 4A-B), which functions to house the sharpened needle tip 106 of the insertion needle 104 to reduce the likelihood of an inadvertent needle stick. FIG. 4A depicts the catheter insertion device 102 in a first or ready for use position, in which the catheter assembly 100 is selectively coupled to the catheter insertion device 102. In particular, the catheter assembly 100, which can include a catheter tube 108 and a catheter hub 110, can be positioned over the insertion needle 104 of the catheter insertion device 102, with a sharpened needle tip 106 of the insertion needle 104 protruding from a distal end of the catheter tube 108. In some embodiments, a protective sheath or needle cover (not depicted) can be operably coupled to either the catheter assembly 100 or the catheter insertion device 102, and positioned over the sharp needle tip 106 to inhibit unwanted needle sticks. The closed system catheter assembly 101, which can include the catheter assembly 100 and catheter insertion device 102, can be provided for use in a sterilized and assembled state, contained within a hermetically sealed package.

Figure 4B:
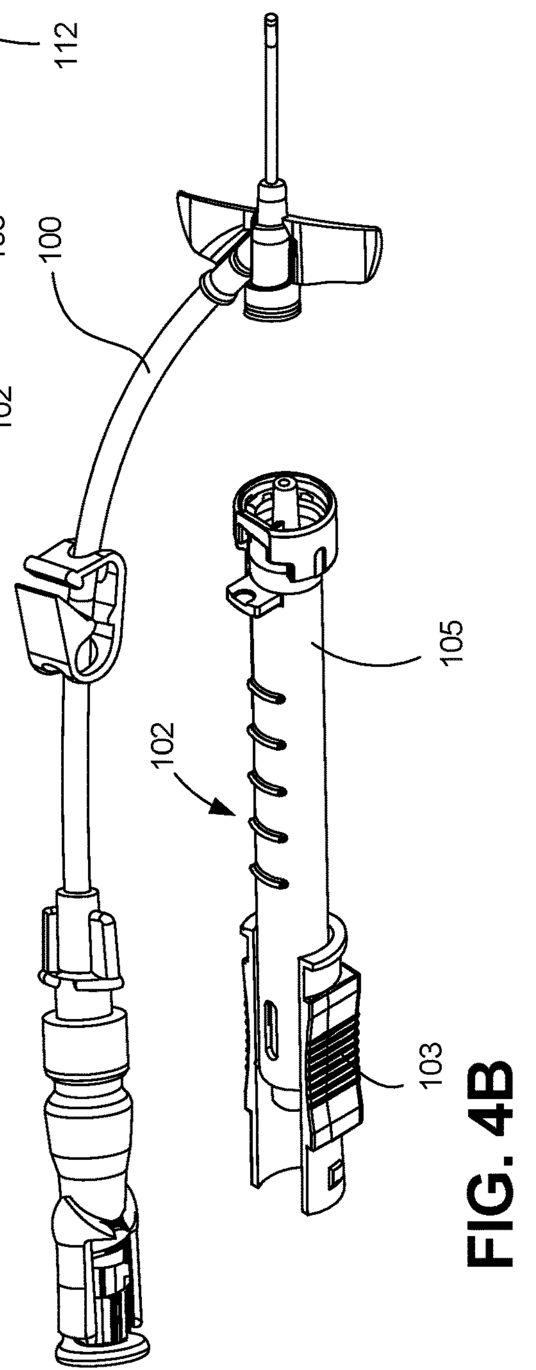
FIG. 4B is a perspective view depicting the intravenous catheter assembly of FIG. 4A, wherein the intravenous catheter assembly is decoupled from the catheter insertion device, and the catheter insertion device is in the needle retracted, safe position.

To insert the catheter tube 108 into a vein of a patient or subject, a clinician first removes the closed system catheter assembly 101 from the packaging. The needle sheath is removed to expose the sharp needle tip 106 of the insertion needle 104 protruding from the distal end of the catheter tube 108. The clinician then punctures an identified site of the subject with the sharpened needle tip 106 and urges the needle 104 forward until the sharpened needle tip 106 enters the vein of the subject. In some embodiments, an initial amount of blood or bodily fluid can pass through a lumen of the needle 104, and enter the catheter assembly 100 and/or catheter insertion device 102 such that the clinician can view the "flashback" of the blood or bodily fluid to confirm entry into the vein. The catheter assembly 100 can then be moved distally over the needle 104, threading the catheter tube 108 into the vein of the subject as the needle 104 is held stationary. With the catheter assembly 100 positioned as desired, the clinician can withdraw the needle 104 by pulling a needle assembly 103 of the catheter insertion device 102 proximally, away from the subject while holding the catheter assembly 100 generally stationary with respect to the subject. The needle assembly 103 can be pulled proximally until the needle 104 of the catheter insertion device 102 is separated from the catheter assembly 100 and safely housed within the needle housing 105 of the catheter insertion device 102, which is referred to as the second or safe position. FIG. 4B depicts the intravenous catheter assembly 100 and the safe position. In the safe position, the clinician can dispose of the catheter insertion device 102 in a sharps container.

It is to be appreciated that the term "distal," as used herein, refers to the direction along an access that lies parallel to the needle 104 of the closed system catheter assembly 101 that is closest to the subject during catheter insertion. Conversely, the term "proximal," as used herein, refers to the direction lying along the axis parallel to the needle 104 that is further away from the subject when the catheter is inserted into the vein of the subject, opposite to the distal direction.

Figure 5A:
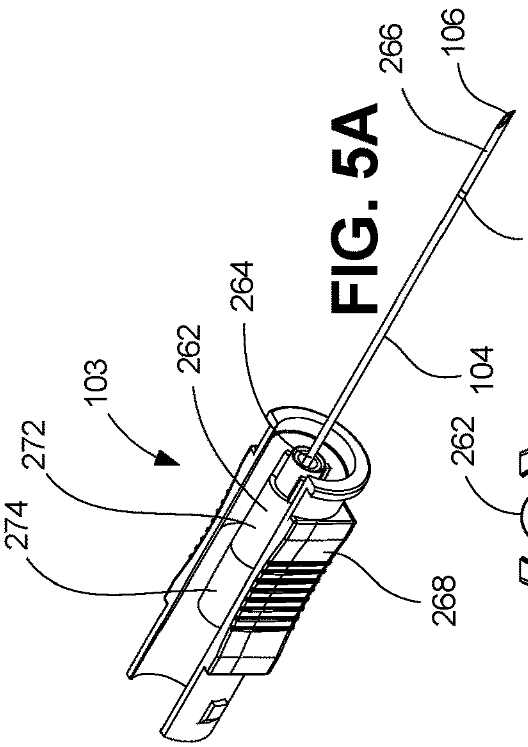
FIG. 5A is a side perspective view depicting a needle assembly of a catheter insertion device in accordance with an embodiment of the disclosure.
Figure 5B:
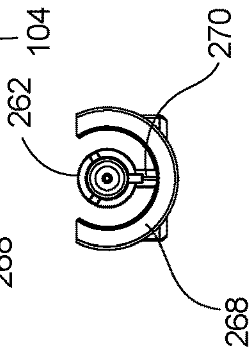
FIG. 5B is a distal end view depicting the catheter insertion device of FIG. 5A.
Figure 5C:
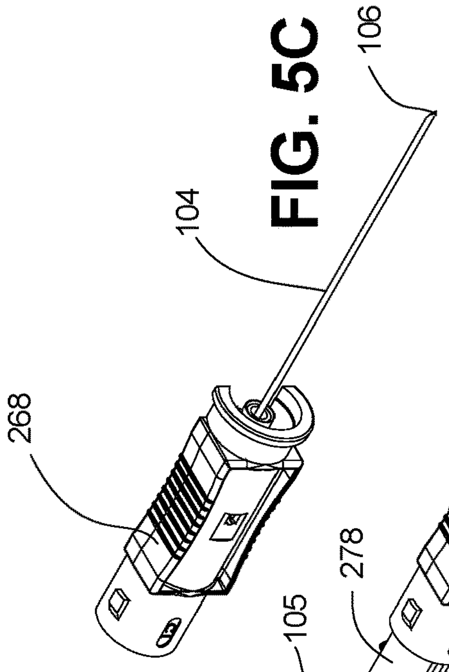
FIG. 5C is a bottom perspective view depicting the catheter insertion device of FIG. 5A.

As depicted in FIGS. 5A-C, the needle assembly 103 can include an insertion needle 104 operably coupled to a needle hub 262. Needle 104 can include an elongate, cylindrically shaped metal structure defining a lumen that extends between a sharpened distal needle tip 106 and a proximal end 264. The sharp needle tip 106 can be constructed and arranged to pierce the skin of a subject during catheter insertion. For example, in one embodiment, the sharp needle tip 106 can include a V-point designed to reduce the penetration force used to penetrate the needle 104 and a portion of the catheter insertion assembly 102 through the skin, tissue, and vein wall of a subject. In one embodiment, the length of the needle 104 can be extended to aid in the insertion of the catheter assembly 100 into obese patients.

Needle 104 can further include a transition 266 that has a different cross-sectional size and/or shape than portions of the needle 104 that lie proximal to the transition 266. Needle transition 266 (alternatively referred to as a needle pump or cannula bump) can be created by crimping opposed sides of the needle 104, or otherwise disrupting the structure of the needle 104, so that the outer surfaces of the needle 104 extend to a larger radial position than other portions of the needle 104, as measured from the center of the needle axis. Transitionals 266 can be formed differently, according to alternate embodiments, such as by adding material to the exterior of the needle, among other ways.

Proximal end 264 of the needle 104 can be operably coupled to the needle hub 262. Needle hub 262 can be connected to a needle g rip 268 positioned on the exterior of the needle housing 105 when assembled thereto for access by a clinician. The needle hub 262 and the needle grip 268 can be operably coupled to one another by a protuberance 270 that can be formed from the same unitary structure as the needle grip 268 and the needle hub 262.

In one embodiment, the needle assembly 103 can be constructed to provide a visual indication of flashback when the sharpened needle tip 106 of the needle 104 enters the vein of a subject. In this embodiment, the needle hub 262 includes a flash chamber 272 in fluid communication with the lumen of the needle 104. When the sharp needle tip 106 enters a vein during catheter insertion, blood or bodily fluid enters the needle lumen from the vein and flows proximally through the needle 104 into the flash chamber 272. The flash chamber 272 can be sealed at one end by a flash plug 274. Flash plug 274 can be made out of an air permeable, hydrophilic material that enables the passage of air, but inhibits the passage of liquid. Air that resides in the needle lumen and flash chamber 272 is therefore pushed through the flash plug 274 by the incoming blood, until the blood reaches the flash plug 274 or is otherwise stopped. Needle hub 262, or portions thereof, can be constructed of a clear or translucent material to enable a clinician to view the presence of blood within the flash chamber 272. In this respect, the clinician can be alerted when the needle has entered the vein of the subject by the presence of blood in the flash chamber 272.

In one embodiment, features of the needle assembly 103, other than a flash chamber 272 can provide an indication that the sharp needle tip 106 has entered the vein of a subject. For example, the needle 104 can include a notch 276. In this embodiment blood flow enters the needle lumen when the sharpened needle tip 106 enters the vein. As blood flows proximally in the needle lumen, some blood passes through the notch 276 and into the annular space that lies between the exterior of the needle 104 and the interior of the catheter tube 108. The presence of blood in the annular space can be viewed by a clinician through clear or translucent portions of the catheter tube 108, providing an indication that the sharpened needle tip 106 is present in a vein.

Figure 6A:
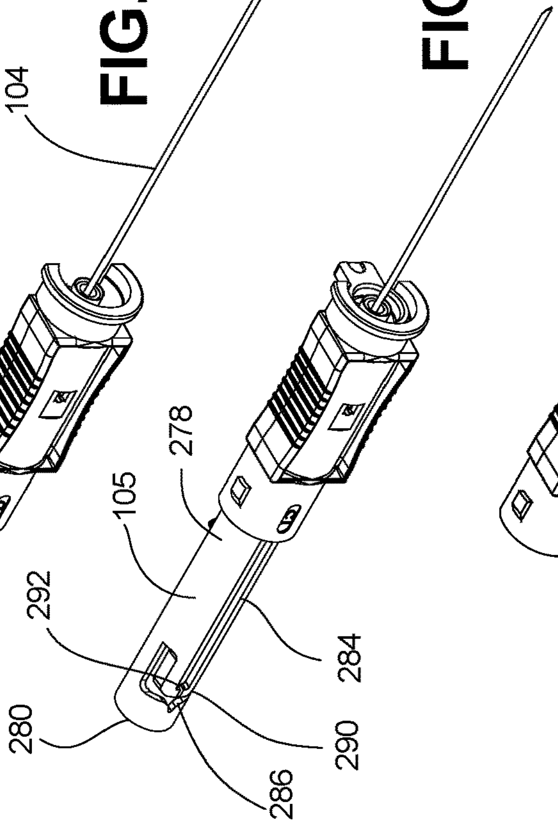
FIG. 6A is a bottom perspective view depicting an interaction between a needle assembly and a needle housing of a catheter insertion device, in accordance with an embodiment of the disclosure, wherein the needle assembly is positioned relative to the needle housing in a distal, engaged, ready for use position.
Figure 6B:
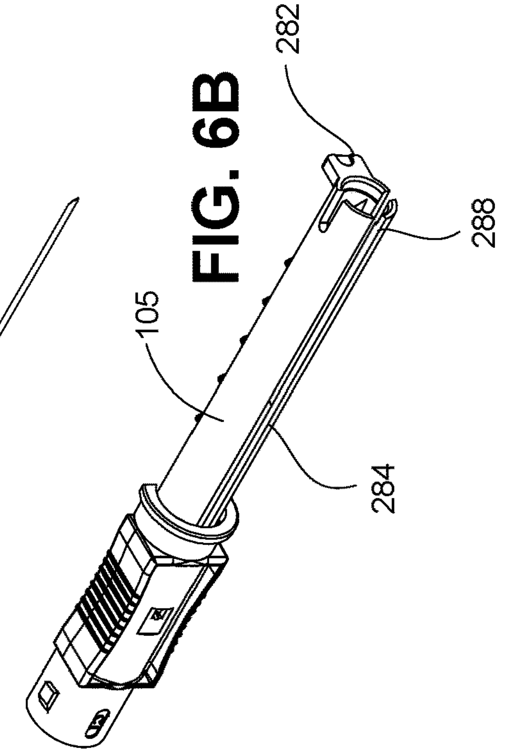
FIG. 6B is a bottom perspective view depicting the interaction between a needle assembly and a needle housing of the catheter insertion device of FIG. 6A, wherein the needle assembly is positioned relative to the needle housing in a proximal, disengaged, safe position.

As depicted in FIG. 6A-B, the needle housing 105 can have a generally cylindrical, elongate body 278 that extends from a proximal end 280 to a distal end 282. A longitudinal slot 284 can be formed along and underside of the needle housing 105 and extend from a proximal slot end 286 near the proximal end 280 of the needle housing 105 to a distal slot end 288 near the distal end 282 of the needle housing 105.

Needle assembly 103 can be slidably coupled to the needle housing 105. For example, the needle assembly 103 can have a "C" shaped cross section conformed to fit around the outer surface of the needle housing 105 in a manner that inhibits the needle assembly 103 from readily separating from the needle housing 105, yet enabling the needle assembly 103 to slide along the longitudinal axis of the needle housing 105 with minimal resistance. In one embodiment, the longitudinal slot 284 can slidably receive the protuberance 270 of the needle assembly 103, with the needle grip 268 positioned outside of the needle housing 105 and at least a portion of the needle hub 262 and the needle 104 positioned internally to the needle housing 105, thereby at least partially housing these features. Accordingly, the needle assembly 103 can be configured to slide along the longitudinal slot 284 to restrict the needle assembly 103 from rotating about the longitudinal axis of the needle housing 105. The protuberance 270 slidably received within the longitudinal slot 284 enables linear movement of the needle hub 262 substantially parallel to the longitudinal axis of the needle housing 105, but restricts the rotational movement of the needle assembly 103 relative to the needle housing 105.

Longitudinal slot 284 can guide the needle assembly 103 in motion with respect to the needle housing 105 between the ready for use position (as depicted in FIG. 6A) and the safe position (as depicted in FIG. 6B). In the ready for use position a portion of the needle 104 extends from the needle housing 105, such that the sharp needle tip 106 of the needle 104 protrudes beyond the needle housing 105. In the safe position, the needle 104 is withdrawn, and the sharp needle tip 106 is housed within the needle housing 105 in a manner intended to reduce or eliminate the likelihood of an inadvertent needle stick.

Catheter insertion device 102 can include a needle lock 290 that engages a needle assembly at a position that is proximal to the sharp needle tip 106 to inhibit the sharp needle tip 106 from being accessed after the needle 104 is used to insert the catheter assembly 100. In this manner, access to the sharp needle tip 106 is inhibited when the needle 104 is in the safe position. Needle lock 290 can thus be configured to interlock the needle assembly 103 to the needle housing 105 in the safe position. In one embodiment, the needle lock 290 can be positioned on a proximal portion of the needle housing 105 at the proximal slot end 286 to engage the protuberance 270. Several different types of locking mechanisms can be used for this purpose. For example, in one embodiment, the longitudinal slot 284 of the needle housing 105 can have a bottleneck 292 defined in it, where the bottleneck 292 of the longitudinal slot 284 generally has a narrower width than the rest of the longitudinal slot 284. Protuberance 270 of the needle assembly 103 can be triangular or wedge like in shape where the apex of the wedge faces the bottleneck 292 when in the ready for use position. When an external force is applied to the needle assembly 103 in an effort to slide it to the safe position, the apex of the wedge of the protuberance 270 can come into contact with the bottleneck 292. Bottleneck 292, which can have a width narrower than that of the protuberance 270, can initially resist movement of the protuberance 270 through the bottleneck 292. However, with sufficient force, the wedge shape protuberance 270 can cause the bottleneck 292 to temporarily deform, thereby enabling the protuberance 270 to pass through the bottleneck 292. For example, in one embodiment, the interaction between the wedge shape protuberance 270 and the bottleneck 292 can create an audible "click" noise, tactile, or visual indication that the protuberance 270 has passed through the bottleneck 292. Thereafter, the protuberance 270 will be unable to pass back through the bottleneck 292 in the opposite direction, and the needle 104 will be locked in the safe position relative to the needle housing 105.

In some embodiments, the catheter insertion device 102 can include an end cap 263 (as depicted in FIGS. 3A-G). The end cap 263 can be coupled to the needle g rip 268 and/or needle hub 262, thereby covering the proximal end 280 of the needle housing 105. End cap 263 can have a proximal end 265 that can provide a surface against which a clinician can press during the catheter insertion procedure, as discussed herein.

Figures 7A, 7B:
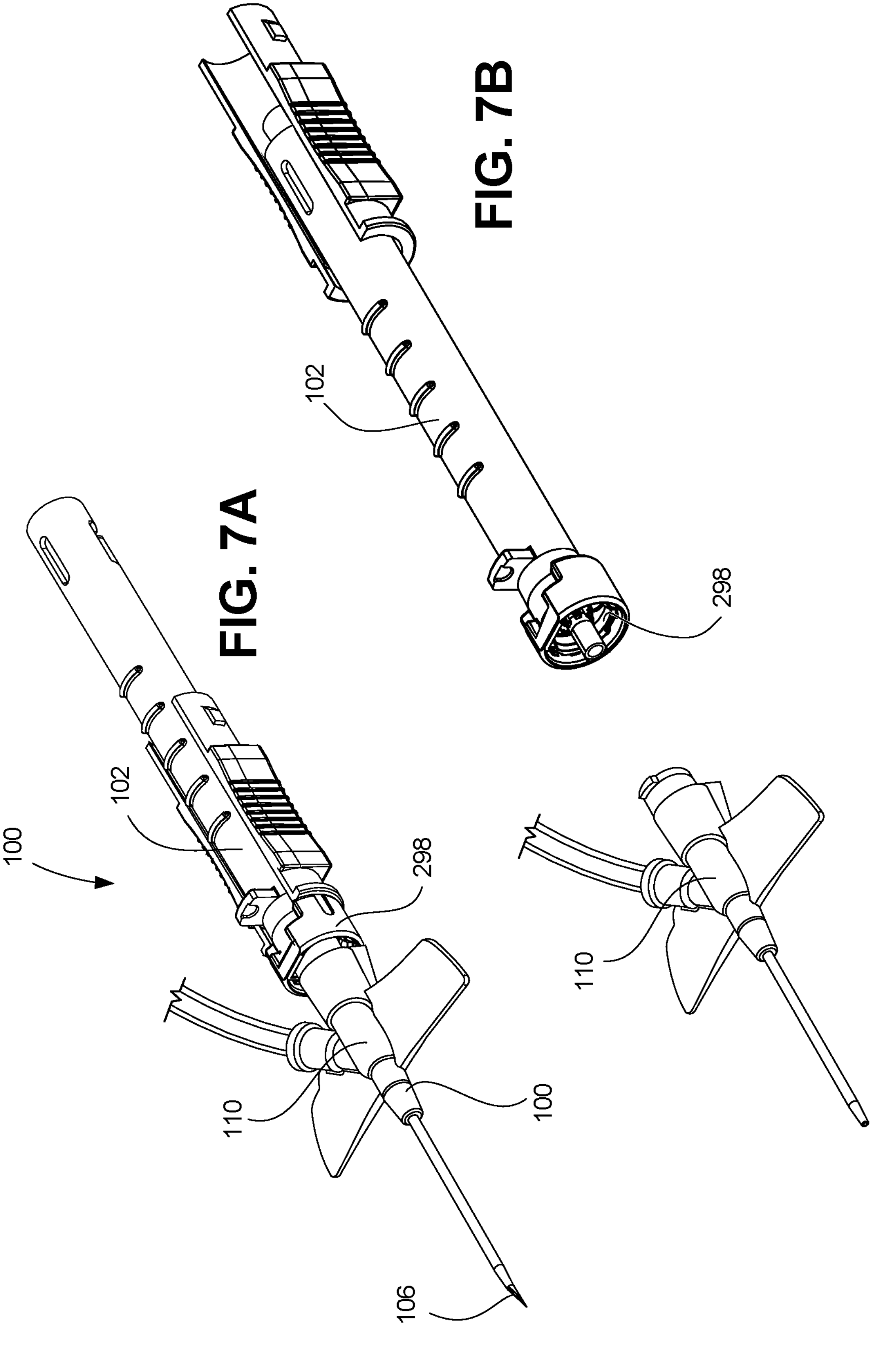
FIG. 7A is a perspective view depicting an intravenous catheter assembly having a passive release mechanism in accordance with an embodiment of the disclosure, wherein the intravenous catheter assembly includes a catheter operably coupled to an catheter insertion device via a passive release mechanism, and wherein the catheter insertion device is in the ready for use position.
FIG. 7B is a perspective view depicting the intravenous catheter assembly of FIG. 7A, wherein the intravenous catheter assembly is decoupled from the catheter insertion device, and the catheter insertion device is in the needle retracted, safe position.

Referring to FIGS. 7A-B, in one embodiment the intravenous catheter assembly 100 can include a passive release mechanism 298. Passive release mechanism 298 can be configured to couple the catheter hub 110 to the catheter insertion device 102 in the ready for use position (as depicted in FIG. 7A) and release the catheter hub 110 from the catheter insertion device 102 and the safe position (as depicted in FIG. 7B). In some embodiments, the passive release mechanism 298 can include one or more catheter hub contacts that inhibit release of the catheter assembly 100 from the catheter insertion device 102 until after the sharp needle tip 106 of the catheter insertion device 102 is in the safe position, where access to the sharp needle tip 106 is inhibited. Release of the catheter assembly 100 from the catheter insertion device 102 can occur during a catheter insertion procedure without the need to perform additional steps aside from safely retracting the needle 104. In this respect, the catheter can be "passively" released by a clinician to obtain "passive" safety. By way of example, the catheter assembly 100 can be released when a clinician pulls on a portion of the catheter insertion device 102 as the clinician withdraws the needle 104 from the catheter assembly 100.

Figure 8B:
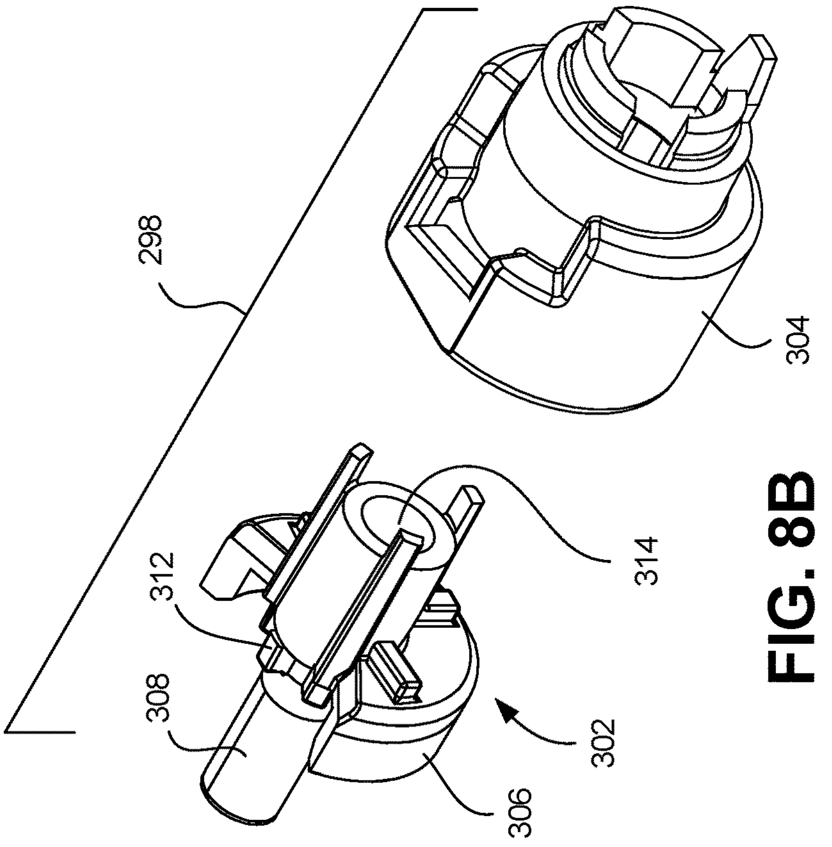
FIG. 8B is an exploded, perspective view depicting a second side of the passive release mechanism of FIG. 8A.
Figure 8A:
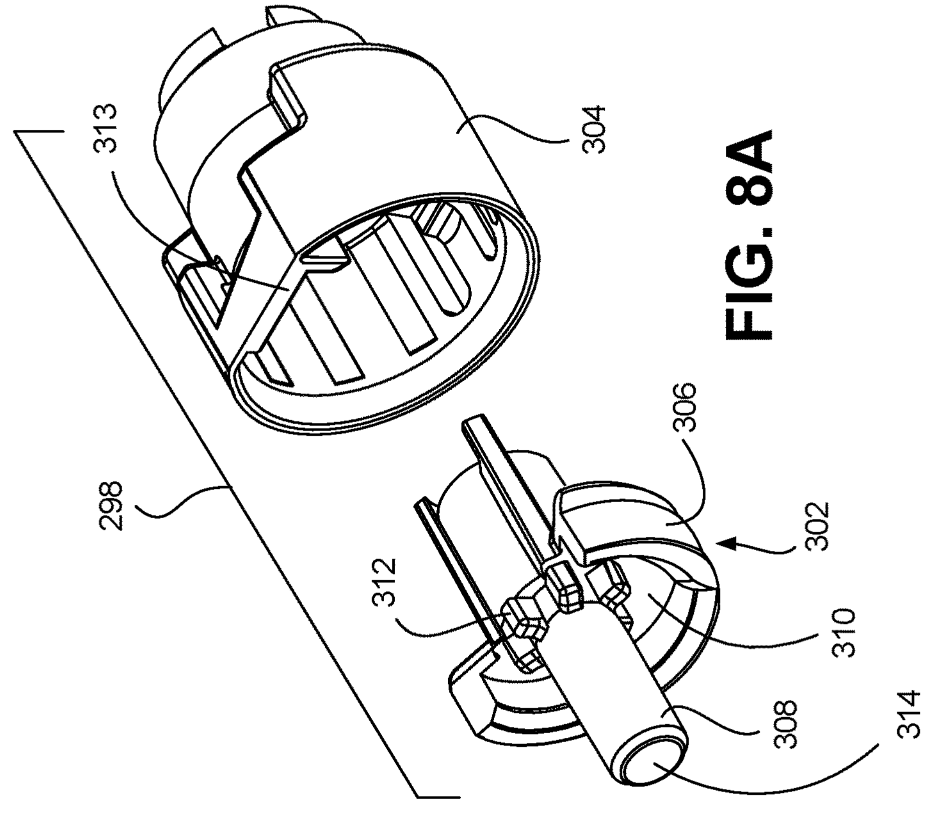
FIG. 8A is an exploded, perspective view depicting a first side of a passive release mechanism in accordance with an embodiment of the disclosure.

Referring to FIGS. 8A-B, an exploded view of a passive release mechanism 298 is depicted in accordance with an embodiment of the disclosure. Passive release mechanism 298 can include a retainer 302 and a collar 304. Retainer 302 can be received within the collar 304, and can include an actuator 306 and a nose 308, such that the actuator 306 and the nose 308 can form a unitary structure. Retainer 302 can be slidably engaged with the collar 304. Retainer 302 can include one or more external hub contacts 310 and one or more interior hub contacts 312, wherein both the external hub contacts 310 and internal hub contacts are configured to contact the catheter hub 110, thereby securely engaging the catheter hub 110 to the passive release mechanism 298 when the actuator 306 is in the distal, engaged position. Additionally, collar 304 can include one or more exterior hub contacts 313.

Figure 9A:
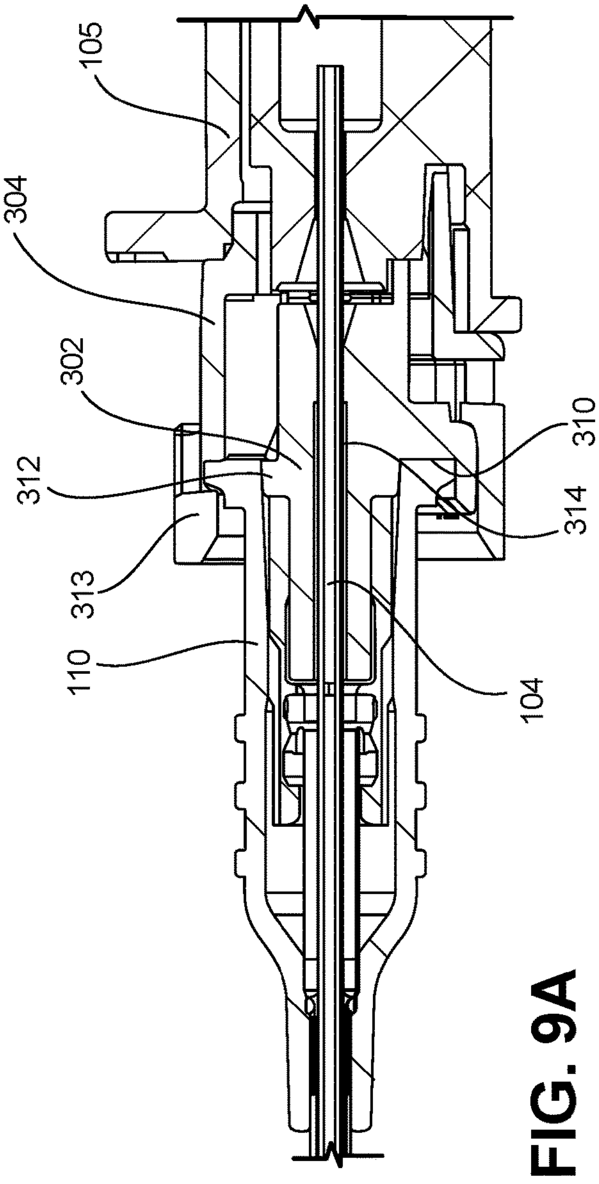
FIG. 9A is a fragmentary, cross-sectional view depicting an intravenous catheter assembly in accordance with an embodiment of the disclosure, wherein the intravenous catheter assembly includes a passive release mechanism having a retainer and collar positioned relative to one another so as to engage a catheter hub in a ready for use position.
Figure 9B:
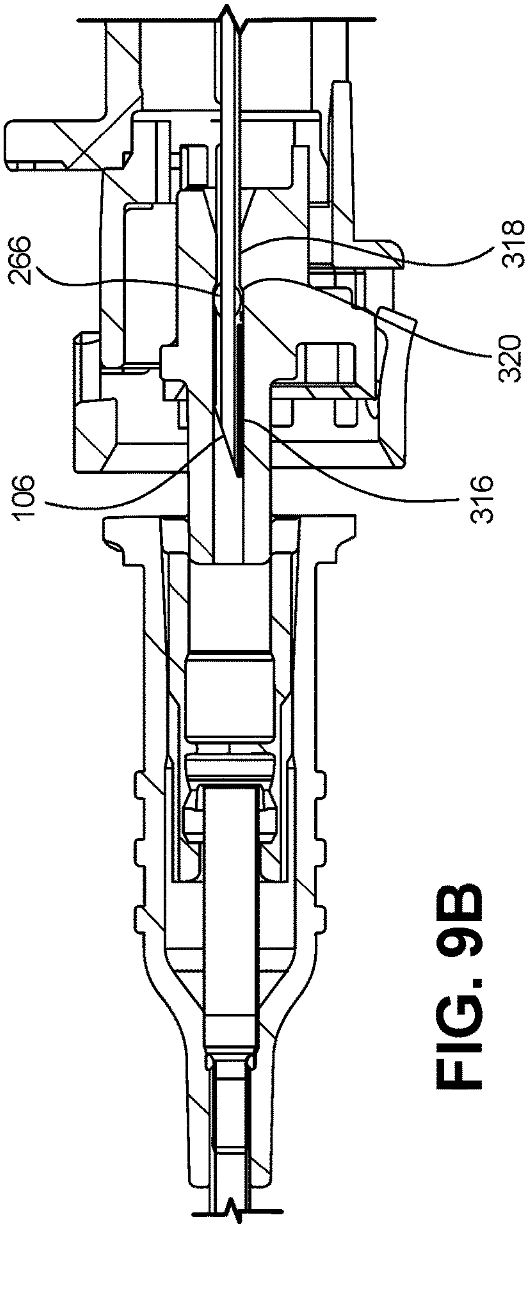
FIG. 9B is a fragmentary, cross-sectional view depicting the intravenous catheter assembly of FIG. 9A, wherein the retainer and collar are positioned relative to one another so as to disengage from the catheter hub in a safe position.

Referring to FIGS. 9A-B, the retainer 302 and the collar 304 can be shaped and sized such that the catheter hub 110 is receivable at least partially within the collar 304 and at least partially over the nose 308. Actuator 306 can be shiftable between a distal, engaged, ready for use position (as depicted in FIG. 9A), wherein the collar 304 can receive a proximal end of the catheter hub 110 and the nose 308 can engage with an interior of the catheter hub 110, and a proximal, disengaged, safe position (as depicted in FIG. 9B), wherein the catheter hub 110 is released from the retainer 302 and the collar 304.

When the nose 308 is in the distal, engaged, ready for use position, a length of the nose 308 that extends within the interior of the catheter hub 110 can be at least twice the diameter of the nose 308. The interior of the catheter hub 110 can be resilient to facilitate disengagement of the catheter hub 110 from the nose 308.

Nose 308 can include a needle passage 314 that can include a wider portion 316 and a narrower portion 318. The wider portion 316 can be distal to the narrower portion 318. The wider portion 316 can be sized so that the needle 104, including the needle transition 266 can be received therein. The narrower portion 318 can be sized to closely approximate the diameter of the needle 104 without the needle transition 266. Accordingly, the needle transition 266 will contact a needle abutment 320 at the juncture of the wider portion 316 and the narrower portion 318 to inhibit further passage of the needle 104. Contact between the needle transition 266 and the needle abutment 320 enables proximal movement of the needle 104 to shift the retainer 302 proximally to the proximal, disengaged, safe position. Nose 308 can be structured to sheath the sharpened needle tip 106 when the sharp needle tip 106 is retracted to the disengaged, safe position.

Shifting of the retainer 302 can occur just prior to the needle assembly 103 reaching the safe position, such that in the proximal, disengaged safe position the exterior hub contacts 310, 313 and/or the interior hub contacts 312 can be disengaged from the catheter hub 110, thereby enabling the catheter hub 110 to be released from the passive release mechanism 298. In particular, when the actuator 306 is in the distal, engaged, ready for use position, a longitudinal axis of the needle assembly 103 and a longitudinal axis of the catheter hub 110 can be substantially coaxial or parallel. When actuator 306 is shifted to the proximal, disengaged, safe position, the catheter hub 110 can be disengaged from the retainer 302 and the collar 304 by angular rotation of the catheter hub 110 relative to the needle assembly 103, such that the longitudinal axis of the catheter hub 110 is not aligned with the longitudinal axis of the needle assembly 103.

The term "passive release mechanism," as used herein, is understood to refer to features of a catheter insertion device 102 that inhibit the release of a catheter assembly 100 until after the catheter insertion device 102 is in the safe position. Some or all of the features of the passive release mechanism 298 can be integral with other components of the catheter insertion device 102. In this respect, the term "passive release mechanism" does not necessarily refer to a component that is separate from the needle assembly 103 and/or needle housing 105. Rather, it is to be appreciated that the passive release mechanism 298, the needle assembly 103, and/or needle housing 105 can comprise the passive release mechanism 298.

II. Catheter Assembly

Catheter assembly 100 generally includes a catheter tube 108 and a catheter hub 110. As depicted in FIG. 2A-G, in one embodiment, the catheter assembly 100 can optionally include a wing assembly 112, an extension tube 114, an extension tube clamp 116, a needleless connector 118, and a vent cap 120. Accordingly, catheter assembly 100 can be a closed system catheter configured to inhibit blood from escaping after withdrawal of the needle 104, thereby reducing the risk of exposure of blood or other bodily fluids to clinicians, particularly a consideration of sensitivity where blood-borne diseases may be present. Additionally, embodiments of catheter assembly 100 can inhibit the introduction of unwanted contaminants into the interior of catheter assembly 100 prior to the connection to an IV fluid supply.

A. Catheter Tube, Hub and Wings

Figure 10A:
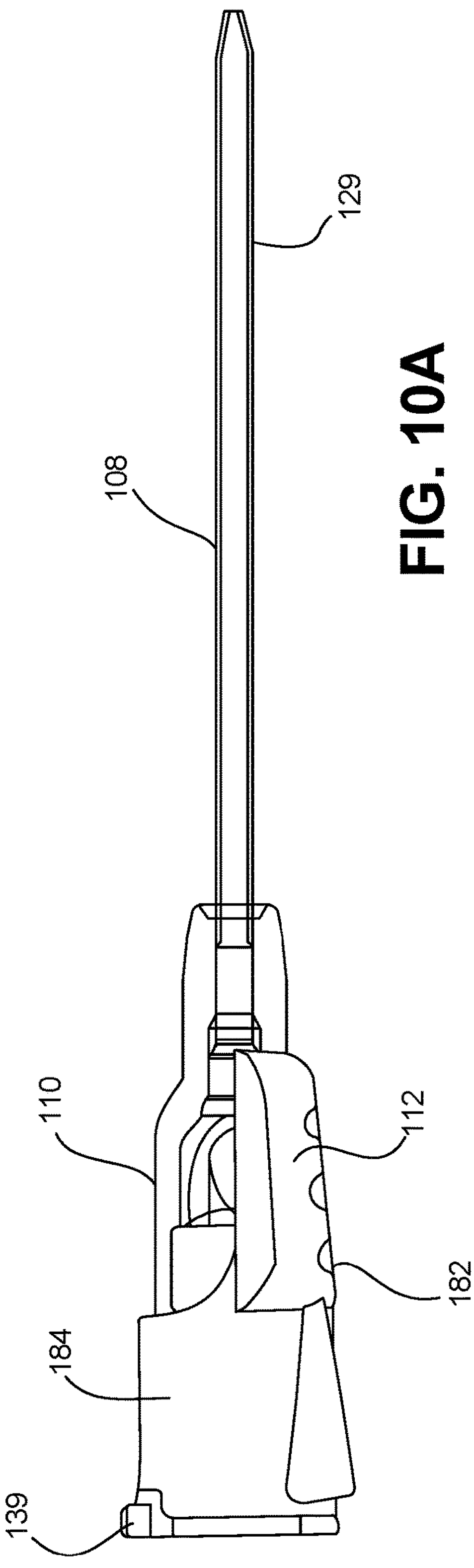
FIG. 10A is a profile view depicting a catheter tube, catheter hub and wing assembly in accordance with an embodiment of the disclosure.
Figure 10B:
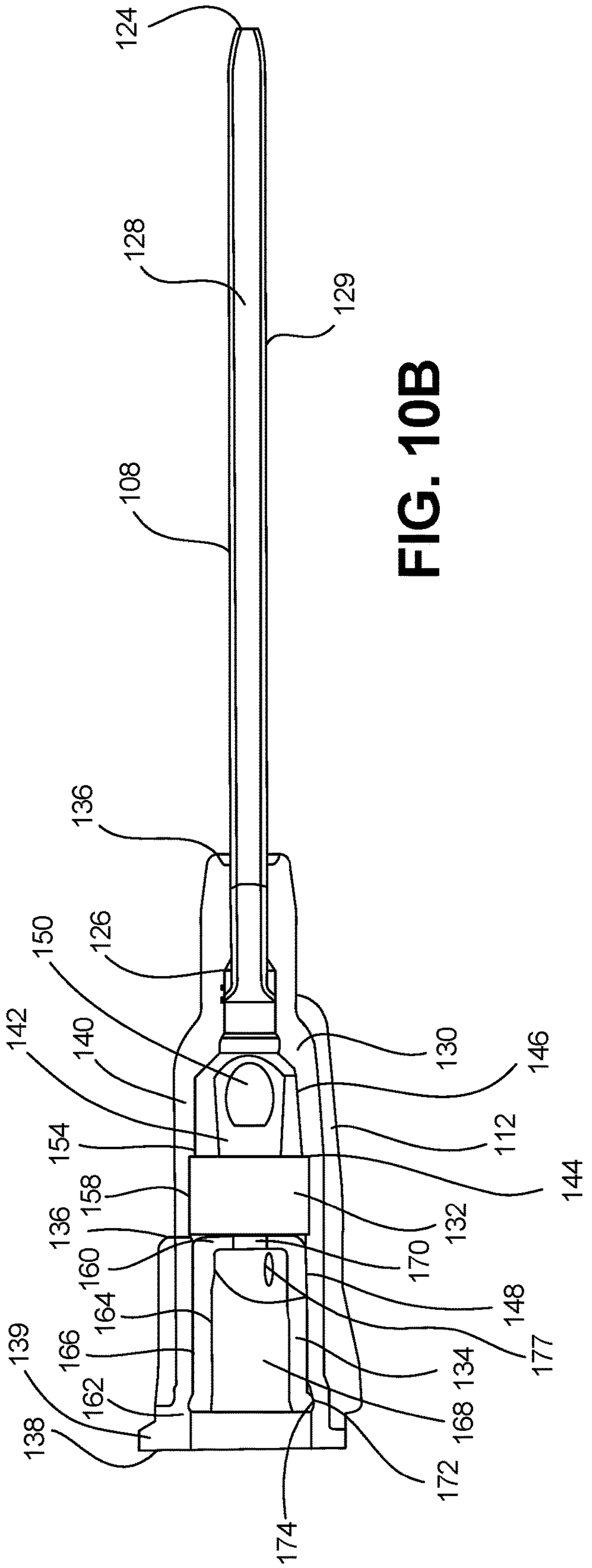
FIG. 10B is a cross-sectional view depicting the catheter tube, catheter hub and wing assembly of FIG. 10A.

Referring to FIGS. 10A-B the catheter tube 108 and catheter hub 110 are depicted in accordance with an embodiment of the disclosure. Catheter tube 108 can extend from a distal end 124 to a proximal end 126, where the catheter tube 108 can be operably coupled to the catheter hub 110. The catheter tube 108 can define a lumen 128 configured to provide a fluid pathway between the vein of a subject and the catheter hub 110. In one embodiment, the catheter tube 108 can include a barium radio opaque line 129 to ease in the identification of the catheter tube 108 during radiology procedures.

Catheter hub 110 can include a catheter hub body 130, a septum 132 and a septum retainer 134. Catheter hub body 130 can have a distal end 136, a proximal end 138 and an internal wall 140 defining a first internal fluid passageway 142 therebetween. In one embodiment, the distal end 136 of the catheter hub body 130 is operably coupled to the proximal end 126 of the catheter tube 108, such that the lumen 128 of the catheter tube 108 is in fluid communication with the first internal fluid passageway 142. In one embodiment, the internal wall 140 further defines a transitional step 144 within the first internal fluid passageway 142 between a smaller diameter portion 146 of the first internal fluid passageway 142 proximal to the distal end 136, and a larger diameter portion 148 of the first internal fluid passageway 142 distal to the proximal end 138.

In one embodiment, the internal wall 140 further defines a side port 150. In one embodiment, the side port 150 is in fluid communication with the first internal fluid passageway 142. In one embodiment, the side port 150 extends away from the first internal fluid passageway 142 and at an oblique angle to the lumen 128 of the catheter tube 108. Side port 150 can provide a connection point to one or more lengths of extension tube 114, so that the inside of the extension tube 114 is in fluid communication with the first internal fluid passageway 142. In one embodiment, the internal wall can further include an extension tube connection point 152.

Septum 132 can have a distal end 154, a proximal end 156 and an outer perimeter 158. Septum 132 can be self-sealing, so that when the needle 104 is withdrawn through the septum 132, any void left by the withdrawn needle 104 will close to provide a seal, and the septum 132 will maintain its fluid impermeability. In one embodiment, the septum 132 is positioned partially within the first internal fluid passageway 142, such that the distal end 154 of the septum 132 abuts up against the transitional step 144, thereby inhibiting forward movement of the septum 132 within the first internal fluid passageway 142. Septum 132 can be constrained about its outer perimeter 158 by the internal wall 140 of the catheter hub body 130. Rearward movement of the septum 132 can be restricted or inhibited by the septum retainer 134.

In one embodiment, the shape of the first internal fluid passageway 142 is configured to promote a more even flow of fluid throughout the first internal fluid passageway 142 to improve flushability of the catheter assembly 100. For example, in one embodiment the first internal fluid passageway is shaped to reduce the occurrence of dead spaces or pockets, thereby reducing the areas where microbial growth is more likely to occur. In one embodiment, the angles of the internal wall 140 of the first internal fluid passageway 142 can be chamfered or filleted to reduce the dead spaces or pockets that may otherwise exist in the interior corners of the internal fluid passageway 142. Additionally, in one embodiment, the septum 132 can be positioned in close proximity to the side port 150 to reduce the dead spaces or pockets and proximal portions of the first internal fluid passageway 142.

Figure 12:
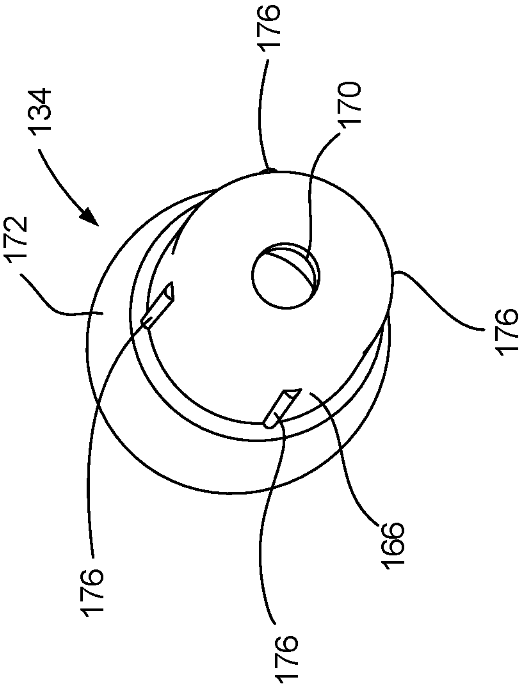
FIG. 12 a perspective view depicting another embodiment of a septum retainer in accordance with the disclosure.

Septum retainer 134 can be configured to secure the septum 132 in position within the first internal fluid passageway 140. In one embodiment, the septum retainer 134 can have a distal end 160, a proximal end 162, an inner wall 164, and an outer wall 166 therebetween. Septum retainer 134 can be at least partially or fully receivable within the first internal fluid passageway 140 of the catheter hub body 130. In one embodiment, the proximal end 162 of the septum retainer 134 is flush with, or recessed with respect to the proximal end 138 of the catheter hub body 130 (as depicted in FIGS. 10B and 12). In one embodiment, the inner wall 164 defines a second internal passageway 168 that can be used to accommodate an insertion needle 104 of the catheter insertion device 102. In one embodiment, the outer wall 166 defines an aperture 170 configured to enable the needle 104 to pass therethrough.

Figure 11:
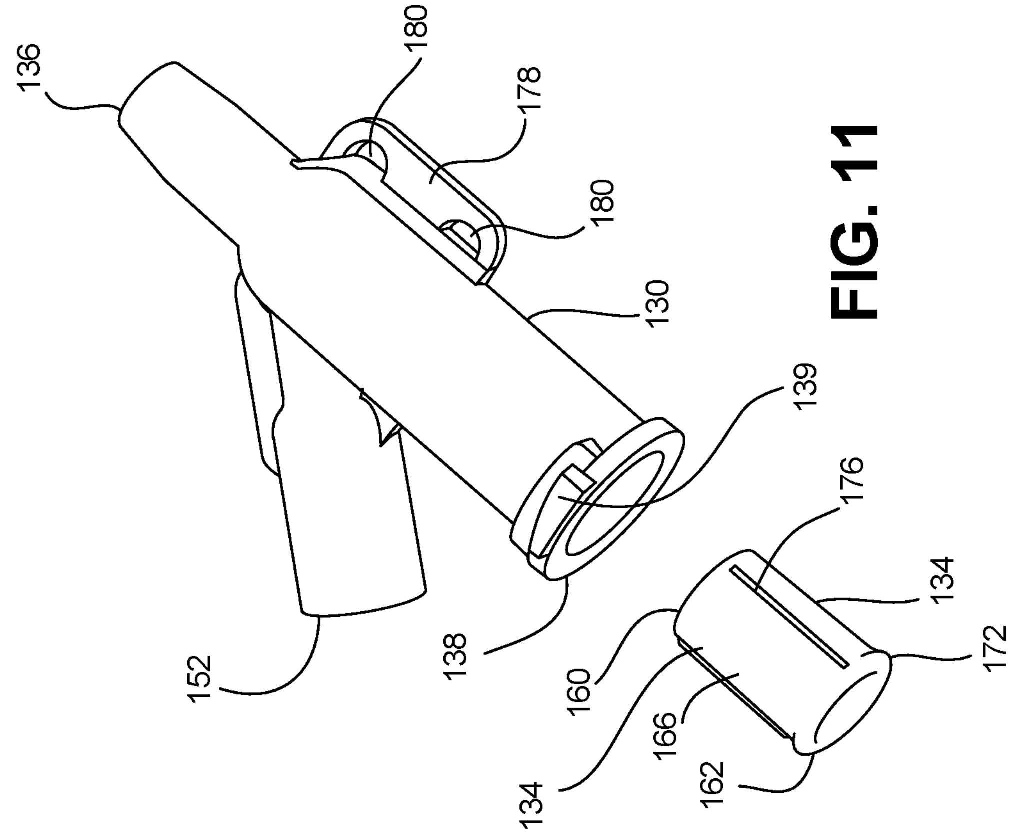
FIG. 11 depicts an exploded, perspective view depicting the catheter hub body and a septum retainer in accordance with an embodiment of the disclosure.

Referring to FIG. 11, an exploded, perspective view of the catheter hub body 130 and a septum retainer 134 is depicted in accordance with an embodiment of the disclosure. Referring to FIG. 12, a perspective view of another embodiment of a septum retainer 134 is depicted in accordance with the disclosure. In one embodiment, the outer wall 166 is shaped and sized to interlock with the internal wall 140 of the catheter hub body 130, thereby coupling the septum retainer 134 to the catheter hub body 130.

Figure 13:
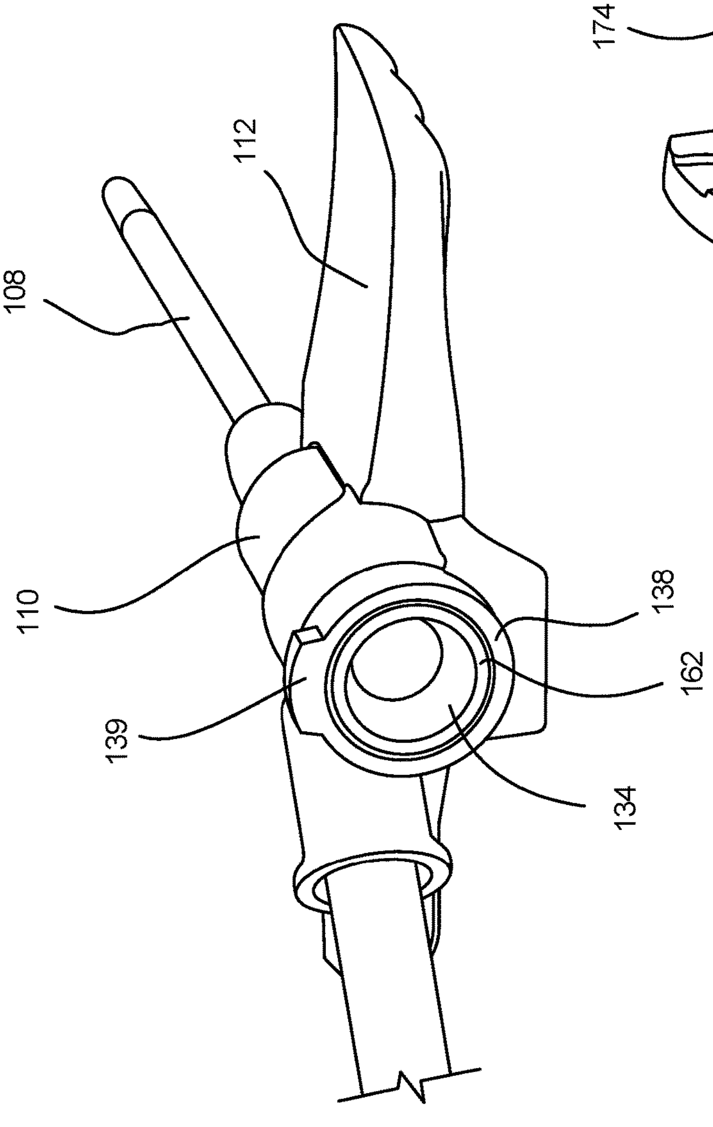
FIG. 13 is a partial view depicting a catheter assembly in accordance with an embodiment of the disclosure.
Figure 14:
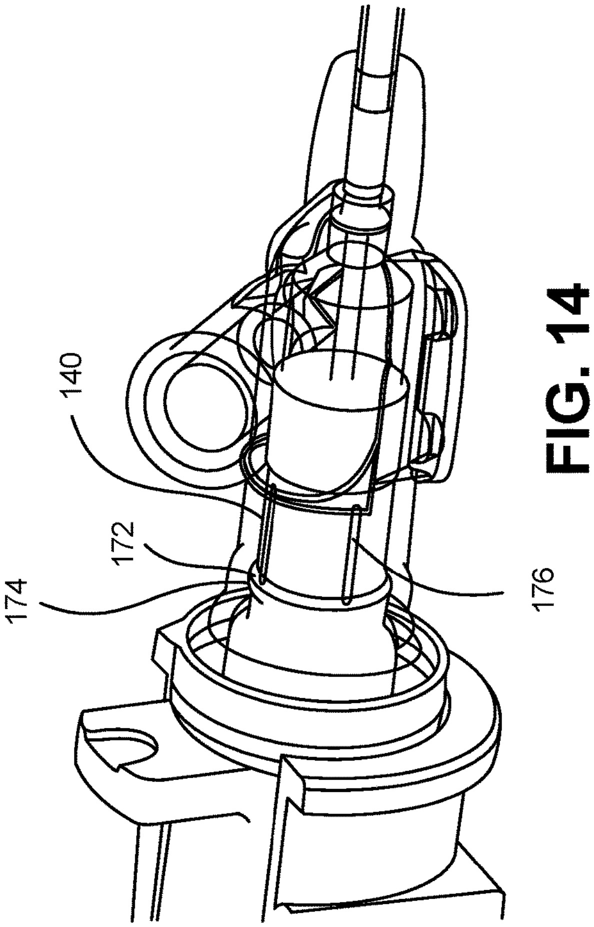
FIG. 14 is a partial, semitransparent view depicting an assembled catheter assembly operably coupled to a catheter insertion device in accordance with an embodiment of the disclosure.

Referring to FIG. 13, a partial view of an assembled catheter assembly 100 is depicted in accordance with an embodiment of the disclosure. Referring to FIG. 14, a partial, semitransparent view of an assembled catheter assembly 100 operably coupled to a catheter insertion device 102 is depicted in accordance with an embodiment of the disclosure. In one embodiment, the septum retainer 134 is snap fit into the catheter hub body 130, without the use of adhesives or ultrasonic welding to couple the septum retainer 134 to the catheter hub body 130. To facilitate a snap fit, in one embodiment, a circumferential retainer ridge 172 can be formed into a portion of the outer wall 166, such that the outer wall 166 and the circumferential retainer ridge 172 are shaped and sized to interlock with the internal wall 140 of the catheter hub body 130. In some embodiments, the internal wall 140 of the catheter hub body 130 can include a circumferential channel 174, configured to receive the circumferential retainer ridge 172 (depicted in FIGS. 10B and 14).

In one embodiment, the septum retainer 134 can include a plurality of lateral ribs 176 positioned on the outer wall 166. Lateral ribs 176 can be configured to provide friction between the septum retainer 134 and the catheter hub body 130, so as to inhibit the septum retainer 134 from rotating relative to the catheter hub body 130 when the septum retainer 134 is assembled with the catheter hub body 130. In one embodiment, the internal wall 140 of the catheter hub body 130 can be configured to at least partially receive a portion of the plurality of lateral ribs 176.

Figure 15:
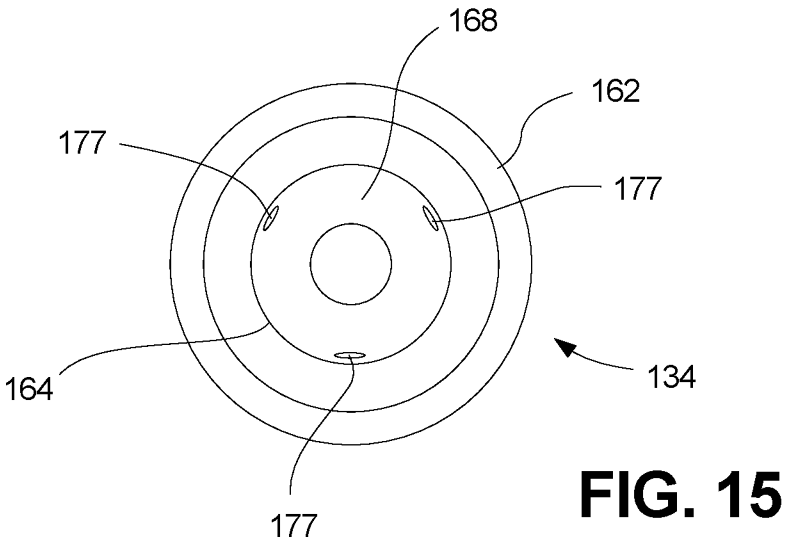
FIG. 15 is an end view of a proximal end depicting a septum retainer in accordance with an embodiment of the disclosure.

Referring to FIG. 15, an end view of the proximal end 162 of septum retainer 134 is depicted in accordance with an embodiment of the disclosure. In one embodiment, the septum retainer 134 can include one or more lateral nubs 177 positioned on the interior wall 164. For example, in one embodiment, three lateral nubs 177 can be positioned on the interior wall 164 and can be configured to protrude inwardly from the interior wall 164 toward the second internal fluid passageway 168.

Figure 16:
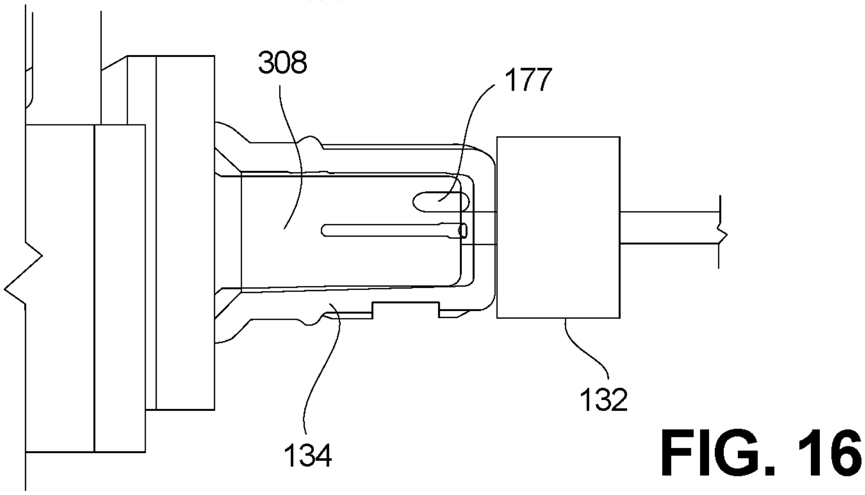
FIG. 16 is a partial, semitransparent view depicting a septum retainer and septum operably coupled to a catheter insertion device in accordance with an embodiment of the disclosure.
Figure 17:
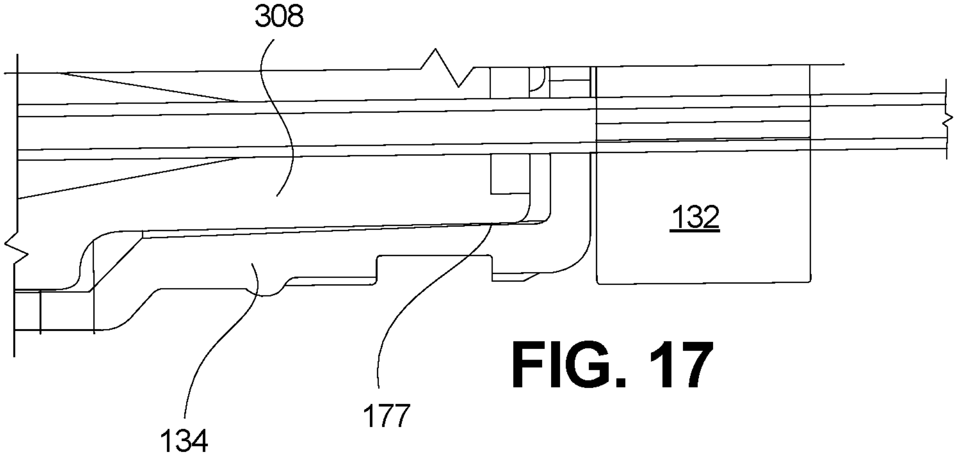
FIG. 17 is a partial, cross-sectional view depicting a septum retainer and a septum operably coupled to a catheter insertion device in accordance with an embodiment of the disclosure.

Referring to FIG. 16, a partial, semitransparent view of a septum retainer 134 and septum 132 operably coupled to a catheter insertion device 102 is depicted in accordance with an embodiment of the disclosure. Referring to FIG. 17, a partial, cross-sectional view of a septum retainer 134 and a septum 132 operably coupled to a catheter insertion device 102 is depicted in accordance with an embodiment of the disclosure. In one embodiment, lateral nubs 177 can be configured to provide friction between the septum retainer 134 and the nose 308 of the passive release mechanism 298, so as to inhibit the septum retainer 134, and the catheter hub 110 generally, from rotating relative to the catheter insertion device 102 when the catheter assembly 100 is coupled to the catheter insertion device 102.

In one embodiment, the friction provided by the lateral ribs 176 is greater than the friction provided by the lateral nubs 177, such that when a rotational force is applied, the septum retainer 134 will rotate relative to the catheter insertion device 102 before the septum retainer 134 will rotate relative to the catheter hub body 130.

In one embodiment, the proximal end 138 of the catheter hub body 130 can include a lug 139. Lug 139 can be configured to orient the catheter hub 110 relative to the catheter insertion device 102, such that the catheter hub 110 can be captured by the passive release mechanism 298. For example, in one embodiment, lug 139 can be configured as a portion of the Luer lock connection.

In one embodiment, the catheter hub body 130 can include one or more ledges 178 configured to provide structural reinforcement as support for a wing assembly 112. In one embodiment, the ledges 178 can define one or more holes 180. The holes 180 can provide improved contact with the wing assembly 112, when the wing assembly 112 is integrally molded onto a portion of the catheter hub body 130. Accordingly, the ledges 178 can serve to both increase the bonding surface between the catheter hub 110 and the wing assembly 112, as well as to serve as a partial structural reinforcement for the wing assembly 112, while at the same time enabling the wing assembly 112 to maintain its flexibility.

Figure 18B:
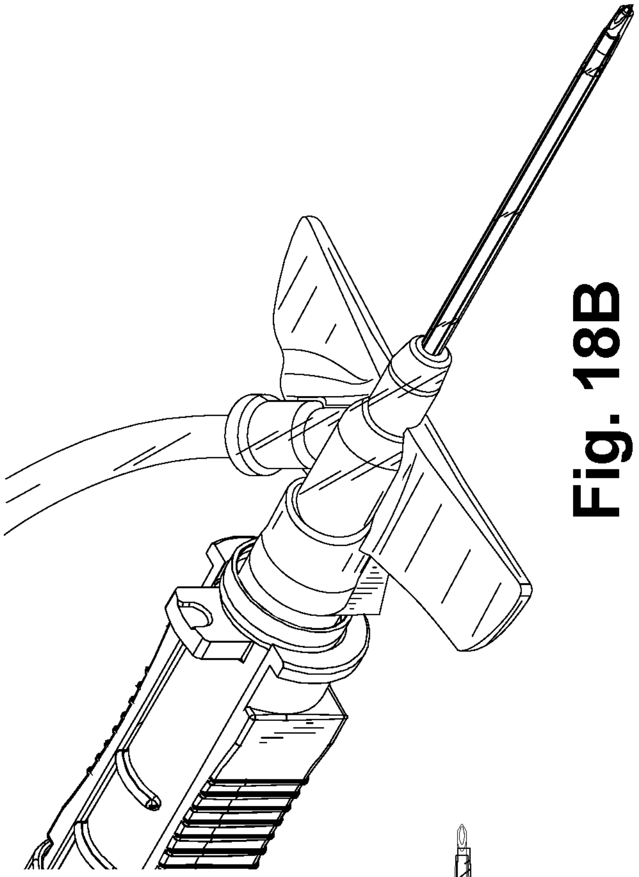
FIG. 18B is a fragmentary, perspective view depicting the intravenous catheter assembly of FIG. 18A.
Figure 18A:
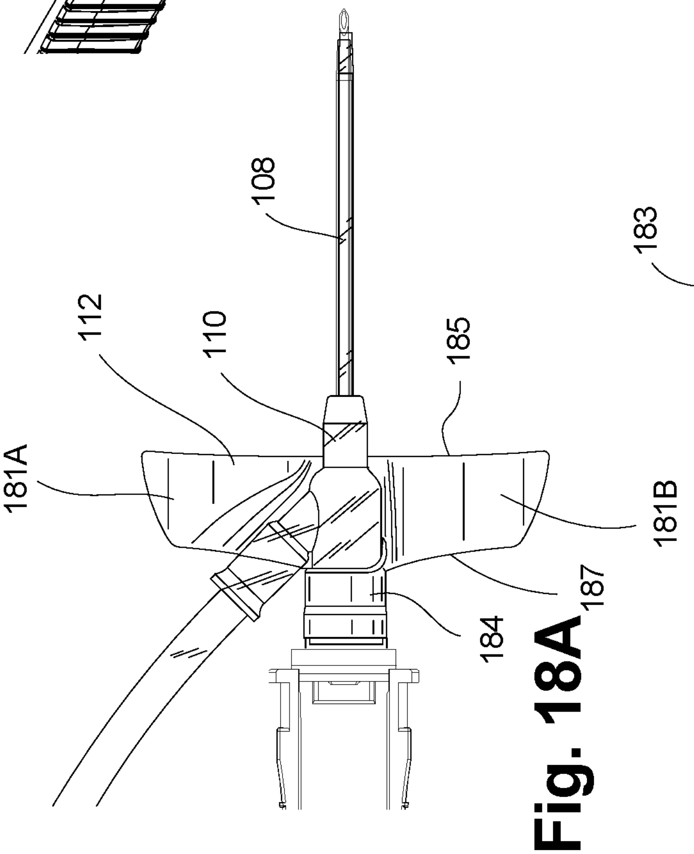
FIG. 18A is a fragmentary, top view depicting an intravenous catheter assembly in accordance with an embodiment of the disclosure.
Figure 18C:
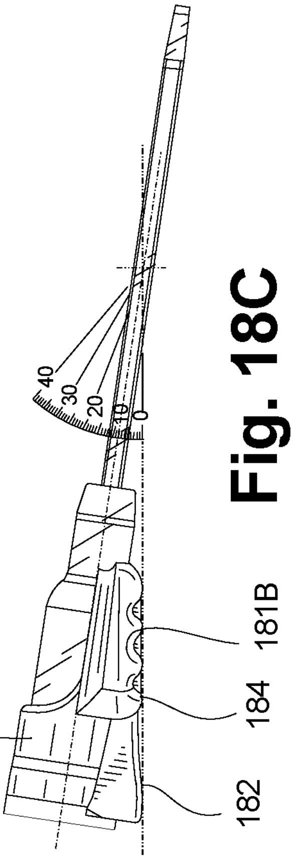
FIG. 18C is a fragmentary, profile view depicting the intravenous catheter assembly of FIG. 18A.

FIGS. 18A-C depict partial views of the intravenous catheter assembly 100 having a wing assembly 112 in accordance with an embodiment of the disclosure. In one embodiment, the wing assembly 112 can include one or more flexible wings 181A/B, a heel portion 182 and a collar 183. The one or more wings 181A/B can generally extend outwardly from a central axis of the catheter tube 108/catheter hub 110, so as to provide an adequate gripping surface for a clinician, as well as an extended surface for aid in securing the catheter hub 110 in place on the patient. The one or more wings 181A/B can have a front edge or distal portion 185 and a rear edge or proximal portion 187. In one embodiment, the distal portion 185 of the wings 181 can form a substantially straight line, extending substantially orthogonal to the axis of the catheter tube 108/catheter hub 110 for improved contact with the skin of the patient. In another embodiment the distal portion 185 of the wings 181 can be concave, so as to form a slight arc, such that the distal edge of the wings 181 extends distally farther than the distal portion of the pair of wings proximal to the catheter tube 108. In one embodiment, a top surface of the wings 181 can define a concave surface configured to aid a clinician in gripping the catheter hub 110

The heel portion 182 can extend from the proximal portion 187 of the wings 181 towards the proximal end 138 of the catheter hub 110. In one embodiment, the heel portion 182 can be a wedge shaped structure configured to support a proximal portion of the catheter hub 110 proximal to the one or more wings 181.

The collar 183 can at least partially wrap around a central axis of the catheter hub 110. For example, in one embodiment, the wing assembly 112 can be integrally molded onto the catheter hub 110, such that the collar at least partially wraps around a proximal portion of the catheter hub 110. In one embodiment, wing assembly 112 can be integrally molded over the one or more ledges 178, with one or more holes 180 defined therein, such that the one or more ledges 187 provide structural reinforcement and support for the wing assembly 112.

As best depicted in FIG. 18C, the bottom surface of the wings 181 and a bottom surface of the heel portion 182 can form a contiguous surface 184. In one embodiment, the contiguous surface 184 can be angled relative to the catheter tube 108, such that the catheter tube 108 can remain in a substantially straight line configuration, without a significant bend or hinge point when the catheter tube 108 is inserted into a patient and the wings 181 are secured to the patient's skin. Sloped contiguous surface 184 enables the wings 181 to be substantially parallel to the skin of the patient, thereby increasing the surface contact between the one or more wings 181 and the patient's skin. In one embodiment, the contiguous surface 184 is angularly offset from the axis of the catheter tube 108 by an angle that ranges between seven and nine degrees. In one embodiment, the contiguous surface 184 is offset from the axis of the catheter tube 108 by approximately eight degrees.

Figure 2A:
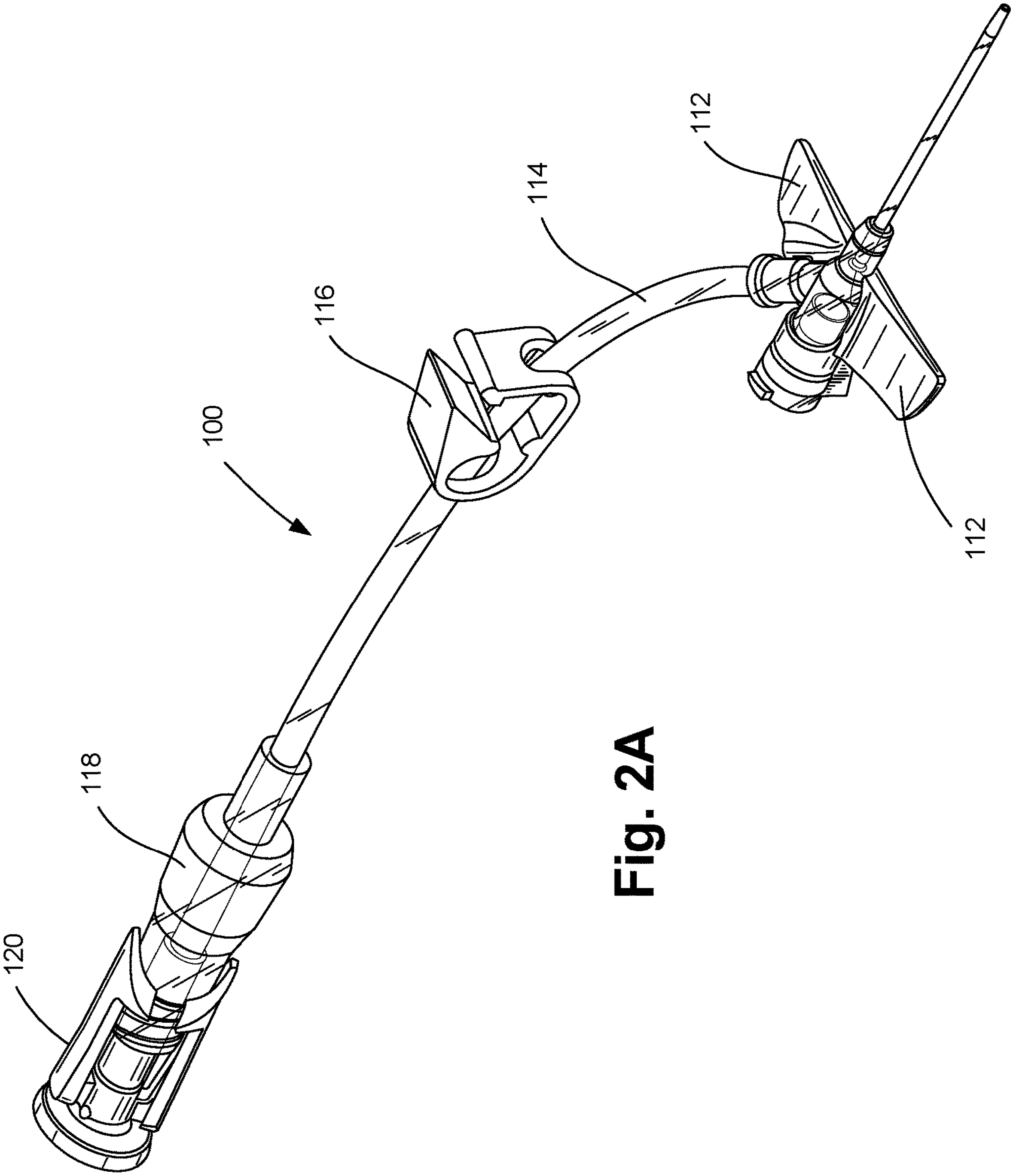
FIG. 2A is a perspective view depicting a catheter assembly, with an extension tube, extension tube clamp, needleless connector and vent cap, in accordance with an embodiment of the disclosure.
Figure 2B:
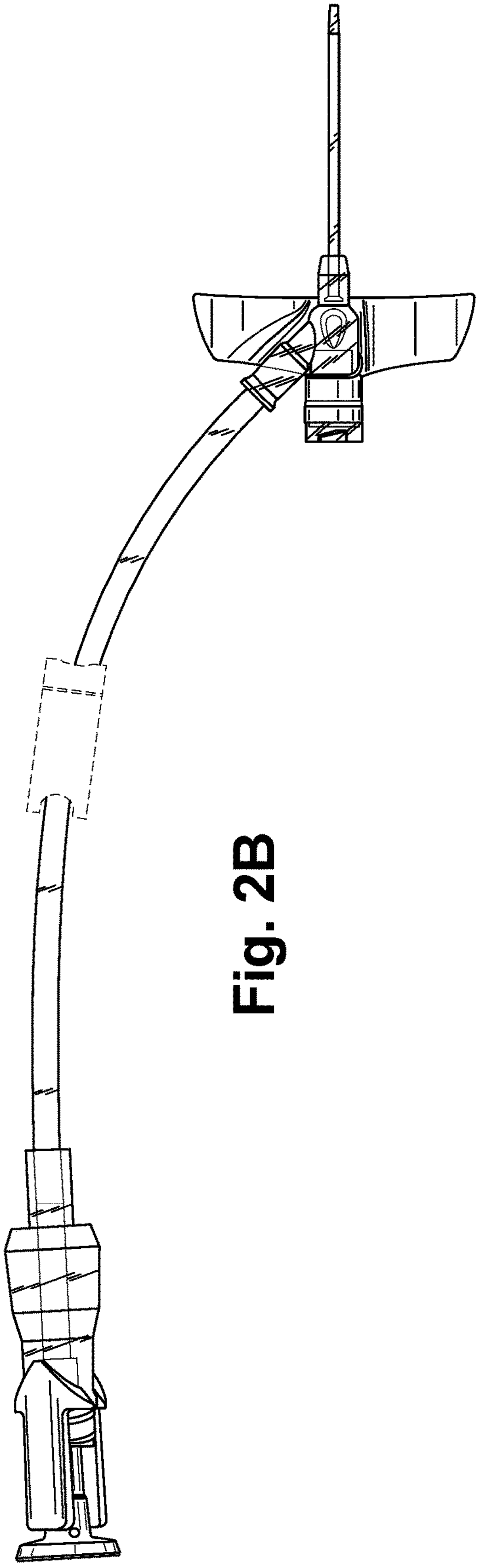
FIG. 2B is a top view depicting the catheter assembly of FIG. 2A.
Figure 2C:
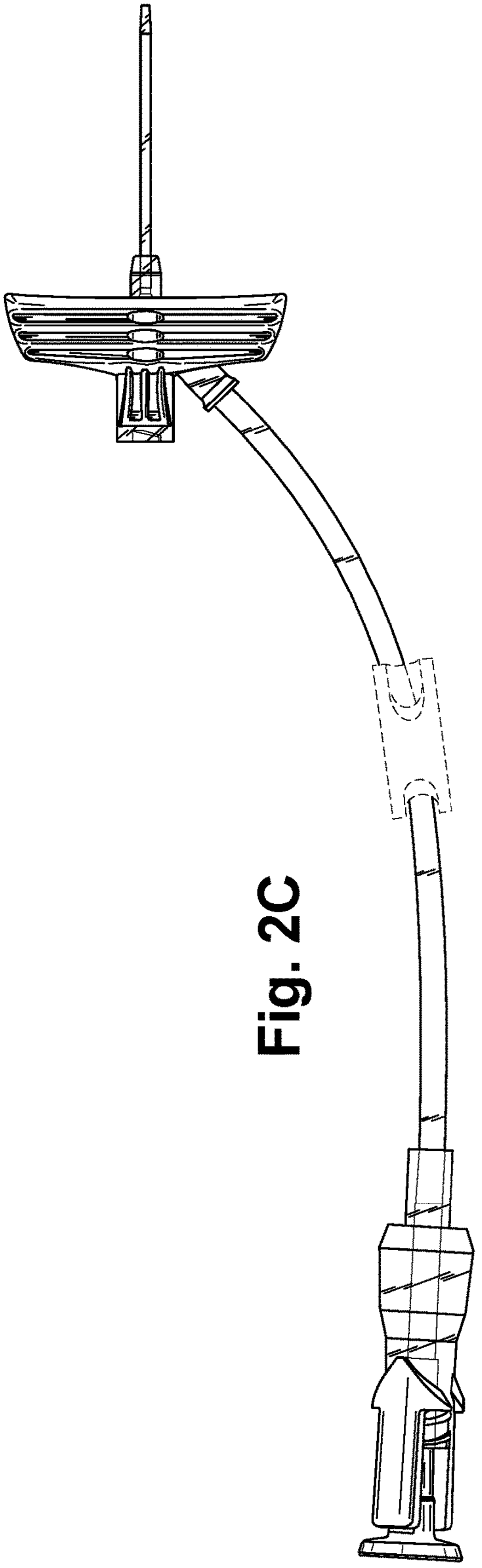
FIG. 2C is a bottom view depicting the catheter assembly of FIG. 2A.
Figure 2D:
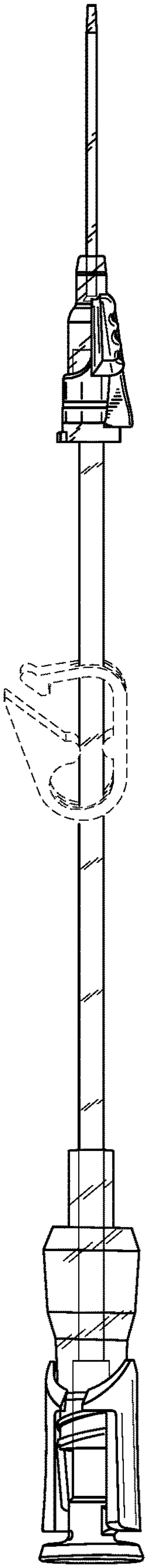
FIG. 2D is a right side view depicting the catheter assembly of FIG. 2A.
Figure 2E:
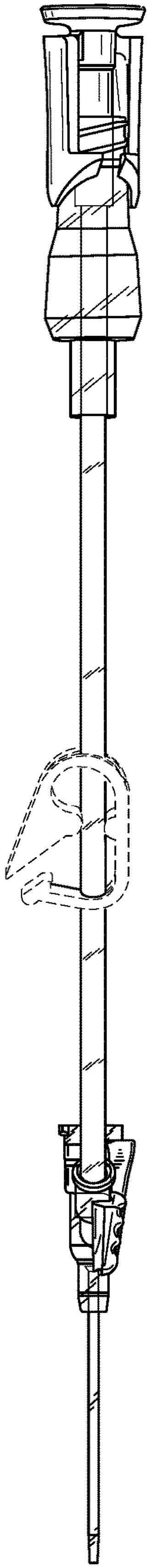
FIG. 2E is a left side view depicting the catheter assembly of FIG. 2A.
Figure 2G:
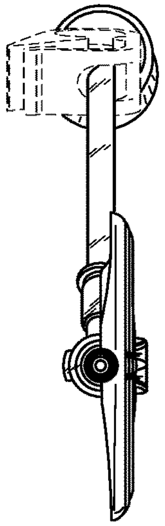
FIG. 2G is a front view depicting the catheter assembly of FIG. 2A.
Figure 2F:
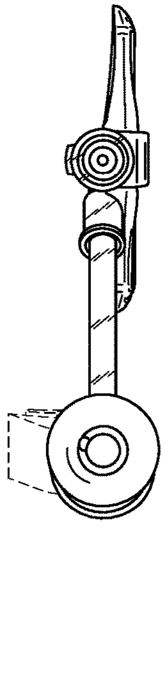
FIG. 2F is a rear view depicting the catheter assembly of FIG. 2A.
Figure 3A:
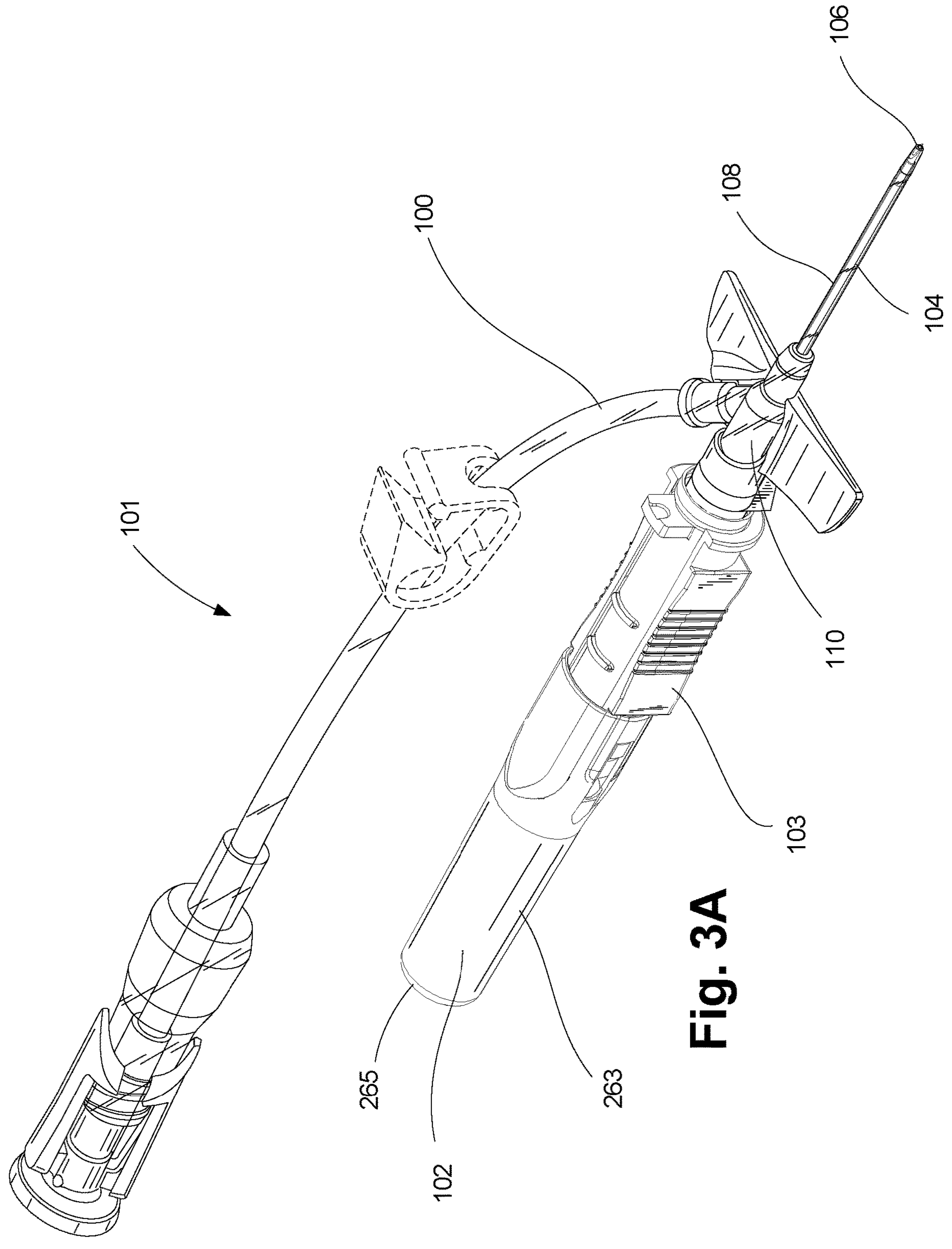
FIG. 3A is a top perspective view depicting a closed system catheter assembly including a catheter assembly operably coupled to a catheter insertion device, in accordance with an embodiment of the disclosure.
Figure 3B:
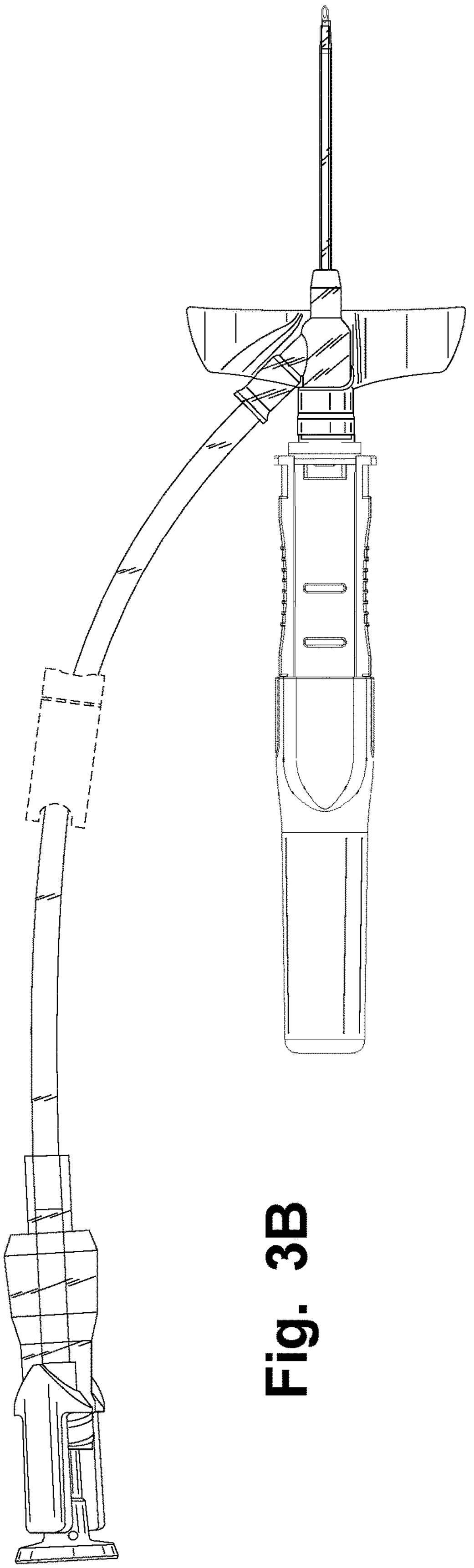
FIG. 3B is a top view depicting the closed system catheter assembly of FIG. 3A.
Figure 3C:
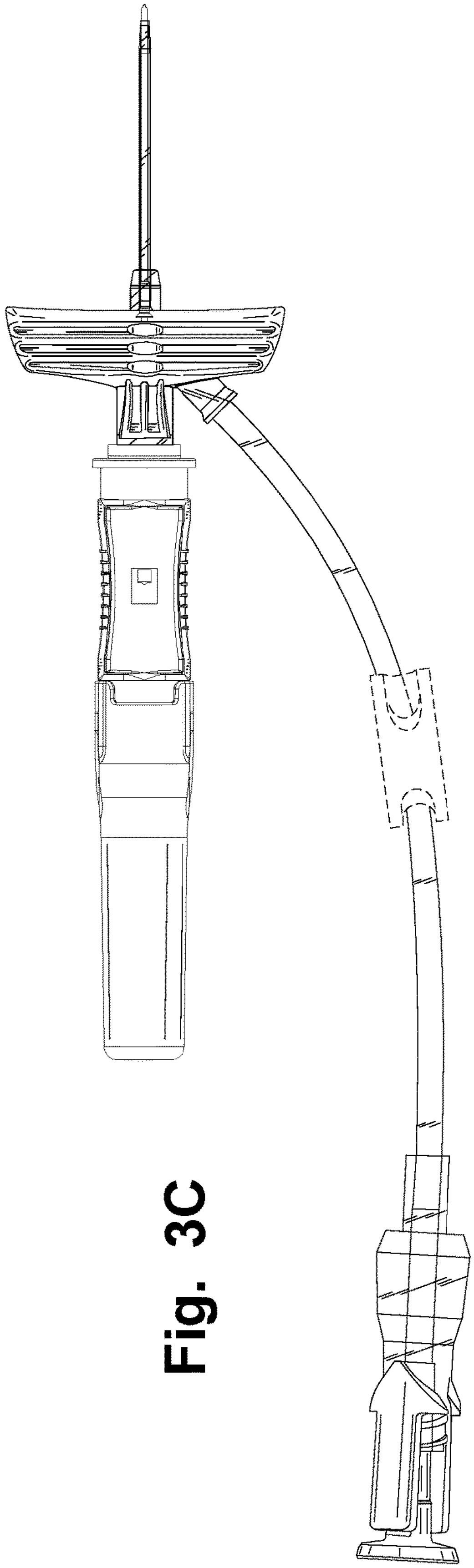
FIG. 3C is a bottom view depicting the closed system catheter assembly of FIG. 3A.
Figure 3D:
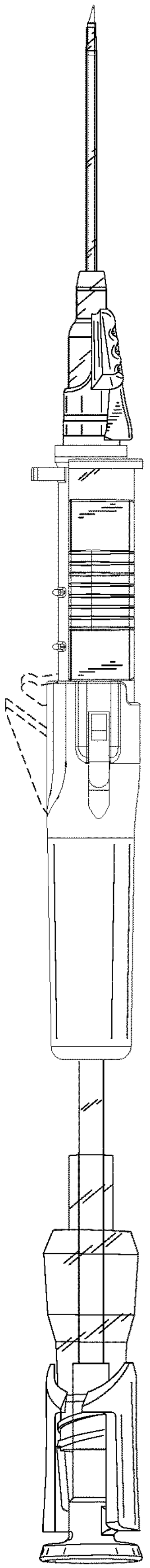
FIG. 3D is a right side view depicting the closed system catheter assembly of FIG. 3A.
Figure 3E:
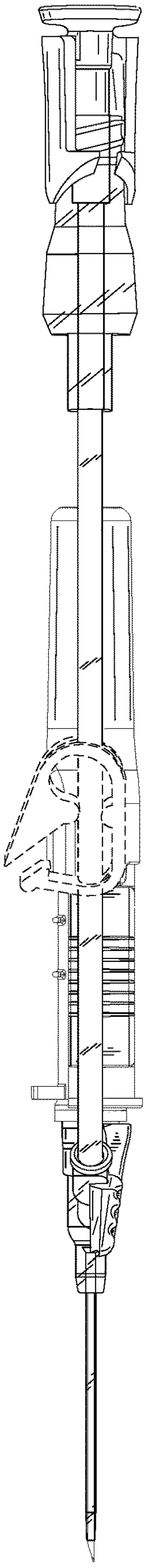
FIG. 3E is a left side view depicting the closed system catheter assembly of FIG. 3A.
Figure 3G:
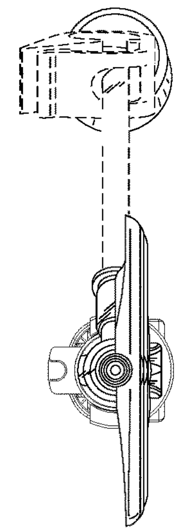
FIG. 3G is a front view depicting the closed system catheter assembly of FIG. 3A.
Figure 3F:
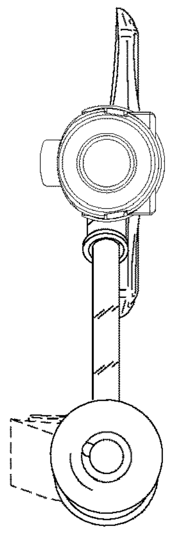
FIG. 3F is a rear view depicting the closed system catheter assembly of FIG. 3A.

For the purpose of conforming to the skin of the patient, the wing assembly 112 can have a lower modulus of elasticity the catheter hub 110, thereby enabling the wing assembly 112 to more easily twist and bend to conform to the contours of the skin of the patient. In one embodiment, the contiguous surface 184 can include a textured pattern, such as a tread, to increase the frictional resistance with the skin of the patient (as best depicted in FIG. 2C). For example, in one embodiment, the contiguous surface 184 can include a plurality of grooves positioned substantially orthogonal to the longitudinal axis of the catheter tube 108 to inhibit the catheter hub 110 from sliding proximally during use. In one embodiment, the contiguous surface 184 can include a plurality of grooves positioned substantially parallel to the longitudinal axis of the catheter tube 108 to inhibit the catheter hub 110 from sliding side to side during use. In one embodiment, the substantially orthogonal grooves can be positioned on the one or more wings 181 and the substantially parallel grooves can be positioned on the heel portion 182. In one embodiment, the textured pattern can aid in preventing perspiration build up, which can occur with a flat or smooth surface. In one embodiment, the textured pattern inhibits the creation of high-pressure areas that may cause discomfort.

B. Septum

One purpose of the septum 132 is to inhibit fluid from passing from the first internal fluid passageway 142 to the second internal fluid passageway 168, or vice versa, in two different configurations. First, the septum 132 can be configured to inhibit fluid passage during catheter assembly 100 insertion and/or when the needle 104 extends through the septum 132. In particular, in some embodiments, a resilient design of the septum 132 can inhibit the septum 132 from retaining a "set" or memory of the opening caused by the needle 104 passing therethrough over the course of the often three or more years that the intravenous catheter assembly 100 may remain in storage prior to use.

Second, the septum 132 can be configured to provide a fluid tight seal under pressure injection, in which the injected medicament can be pressurized to 300 psi or greater, up to 325 psi or greater, or up 350 psi or greater, according to various example embodiments. Septum 132 can also maintain a fluid tight seal under increased flow rates, in which the injected medicament can be administered at up to a rate of 3 mL per second or up to 5 mL per second, according to various example embodiments.

Additionally, while the septum 132 can be configured to provide good sealing properties to inhibit fluid from passing from the first internal fluid passageway 142 to the second internal fluid passageway 168, it can also enable the needle 104 to be retracted without undue resistance, or "drag" force between the interaction of the needle 104 and the septum 132 as the needle 104 is retracted. Accordingly, septum 132 can create a balance between good sealing properties and the reduction of frictional drag on the needle 104 as it is retracted into the safe position.

In one embodiment, the septum 132 is sized to fit within the first internal fluid passageway 142 to create a fluid tight seal with the internal wall 140 to inhibit fluid within the lumen 128 or the first internal fluid passageway 142 from escaping through the proximal end 138 of the catheter hub body 130. In one embodiment, the septum 132 is constructed of a flexible, fluid impermeable material. For example, the septum 132 can be constructed of silicone, isoprene, or other flexible materials. The septum 132 may be radially compressed within the catheter hub body 130 to promote a seal with the catheter hub body 130 and/or the insertion needle 104 when present in the septum 132. According to some embodiments, the septum is compressed up to 10% by volume, up to 15% by volume, up to 20% by volume, or even greater.

Figure 19A:
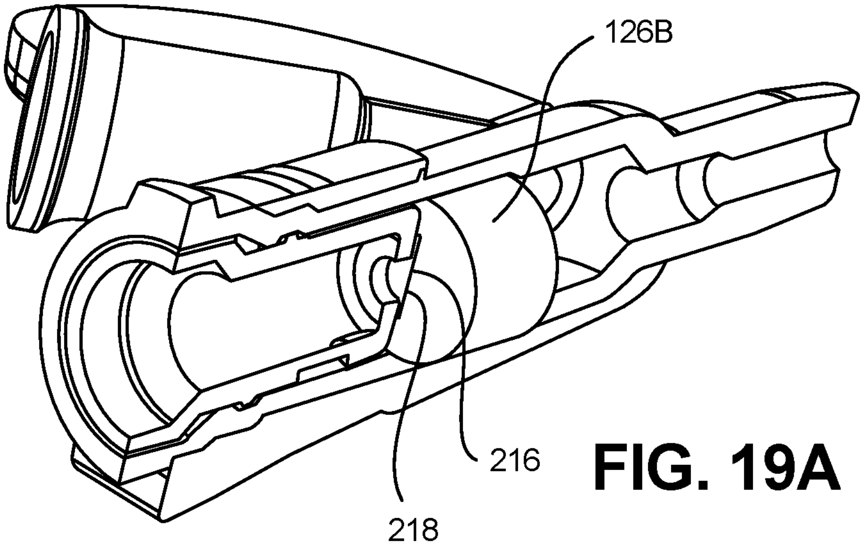
FIG. 19A is a partial cross sectional view depicting a catheter hub, septum retainer and a septum in accordance with an embodiment of the disclosure.
Figure 19B:
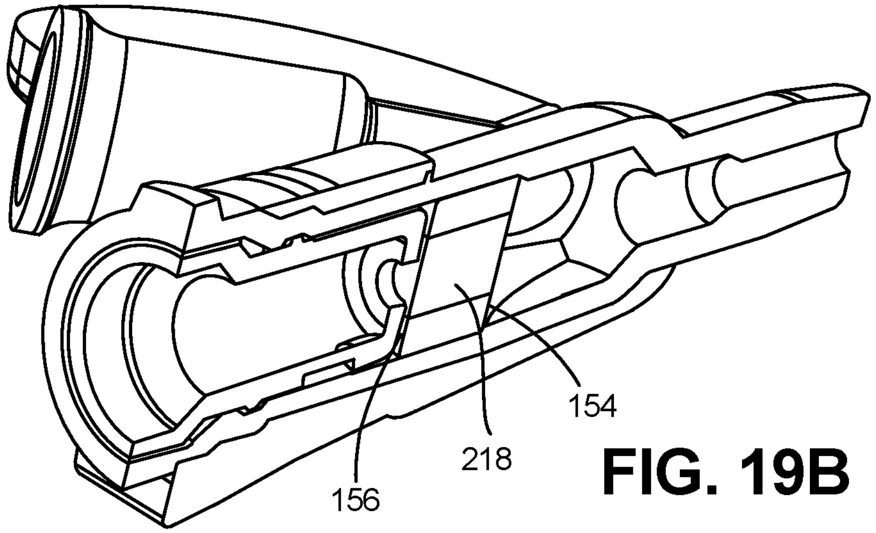
FIG. 19B is a cross sectional view depicting the catheter hub, septum retainer and septum of FIG. 19A.
Figure 20:
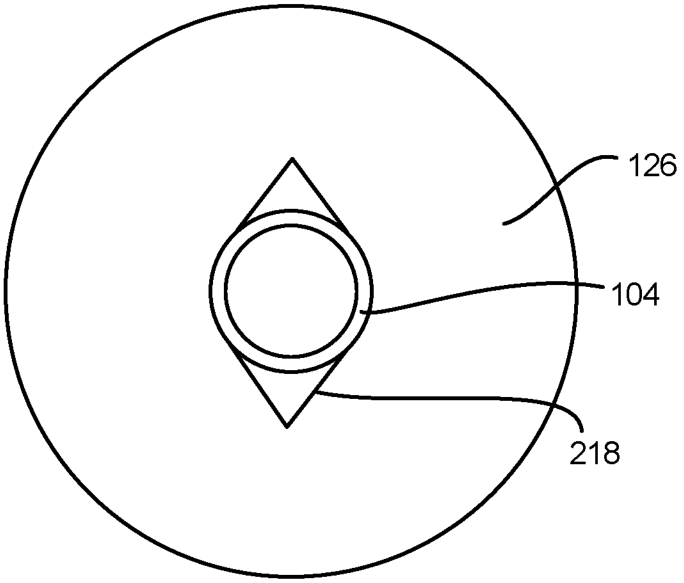
FIG. 20 is an end view depicting a septum having a slit with a needle passing therethrough in accordance with an embodiment of the disclosure.
Figure 21A:
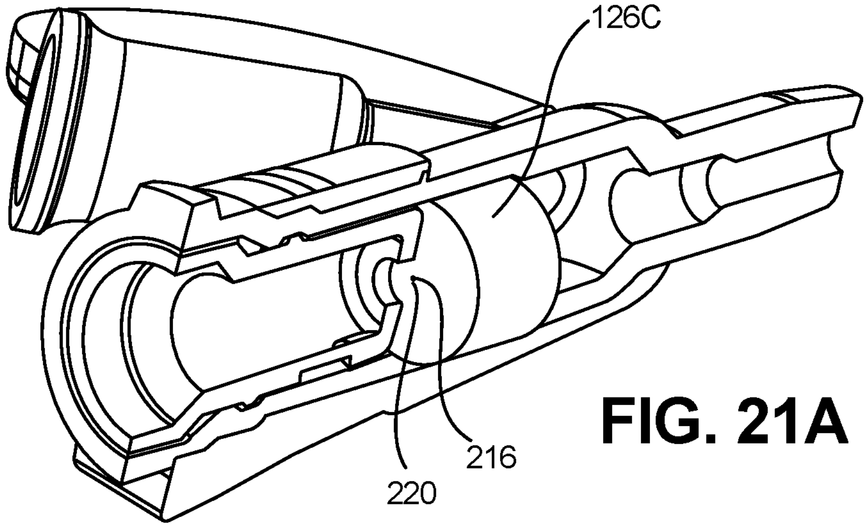
FIG. 21A is a partial cross sectional view depicting a catheter hub, septum retainer and a septum in accordance with an embodiment of the disclosure.
Figure 21B:
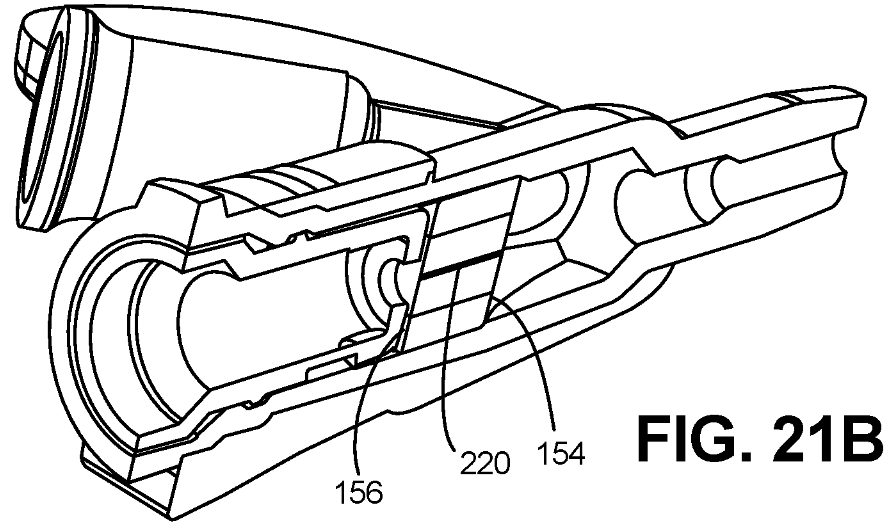
FIG. 21B is a cross sectional view depicting the catheter hub, septum retainer and septum of FIG. 21A.

Referring to FIGS. 19A-B, septum 126B can have an internal surface 216 defining a slit 218 passing from the distal end 154 to the proximal end 156. In one embodiment, the slit 218 can be configured to enable an insertion needle to pass therethrough. Referring to FIG. 20, an end view of a septum 126B having a needle 104 passing through slit 218 is depicted in accordance with an embodiment of the disclosure.

During catheter insertion, needle 104 slides relative to the septum 126B through slit 218. The configuration of the slit 218 generally provides a reduced amount of frictional resistance or drag force in comparison to conventional septum designs. The reduction in drag force is due in part to the "cat's-eye" shape formed by the slit 218 when the needle passes therethrough. The width and/or configuration of the slit 218 can affect the degree to which the cat's-eye shape is formed.

Referring to FIGS. 16A-B, septum 126C can have an internal surface 216 defining an aperture 220 passing from the distal end 154 to the proximal end 156. In one embodiment, the aperture 220 can be configured to enable an insertion needle 104 to pass therethrough. The configuration of the aperture 220 generally provides good sealing properties in comparison to conventional septum designs.

Figure 22A:
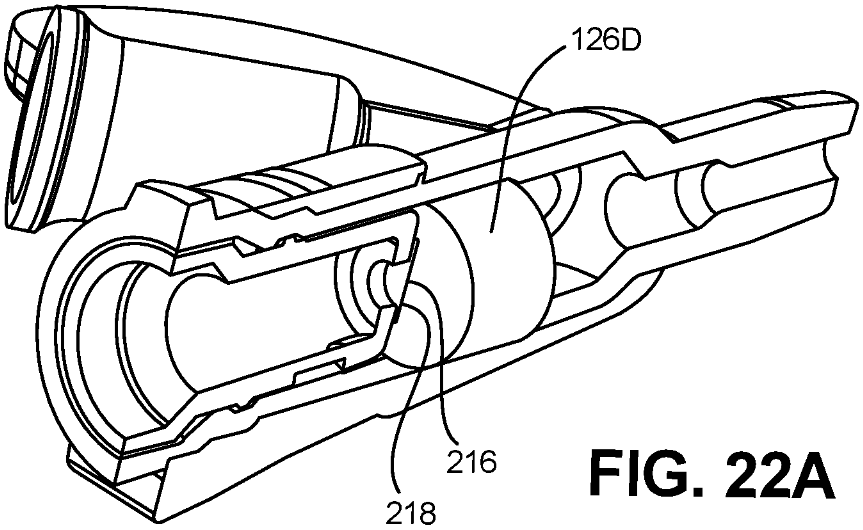
FIG. 22A is a partial cross sectional view depicting a catheter hub, septum retainer and a septum in accordance with an embodiment of the disclosure.
Figure 22B:
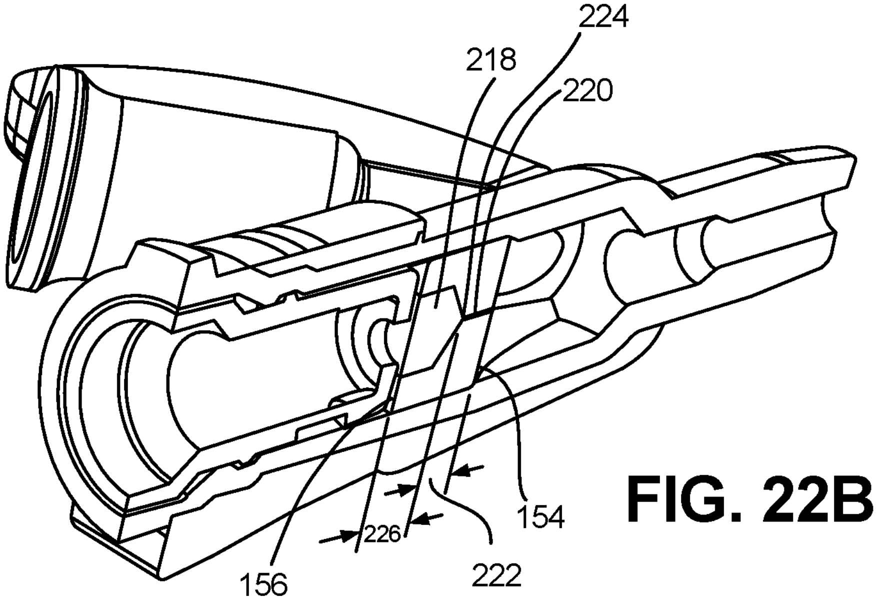
FIG. 22B is a cross sectional view depicting the catheter hub, septum retainer and septum of FIG. 22A.
Figure 23A:
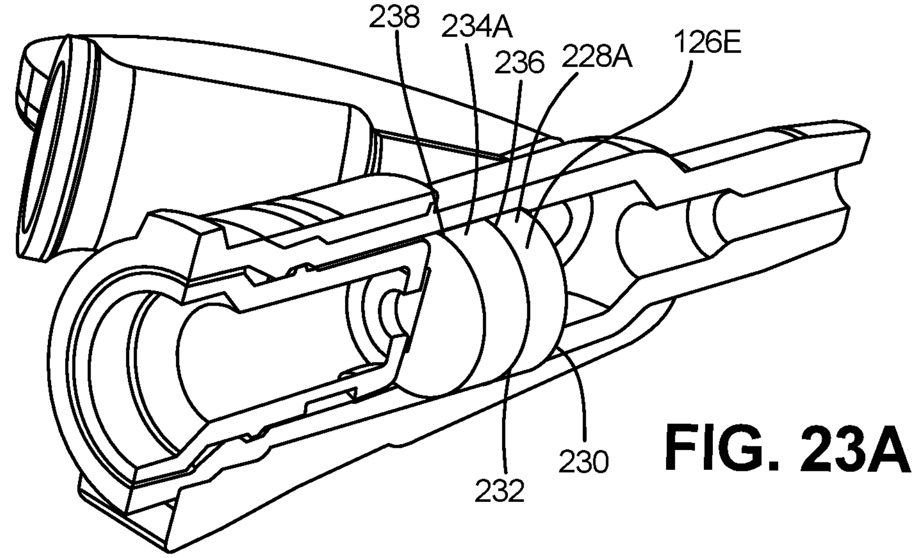
FIG. 23A is a partial cross sectional view depicting a catheter hub, septum retainer and a septum in accordance with an embodiment of the disclosure.
Figure 23B:
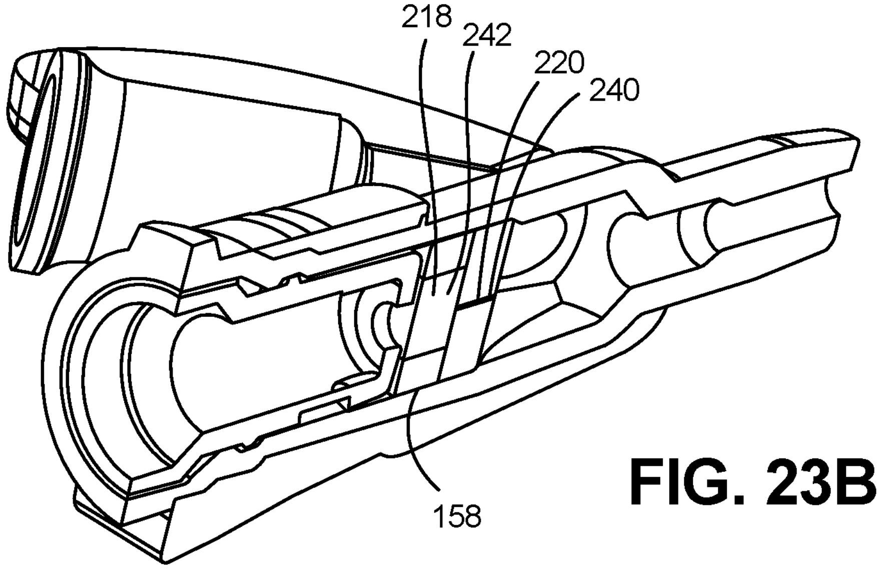
FIG. 23B is a cross sectional view depicting the catheter hub, septum retainer and septum of FIG. 23A.
Figure 24A:
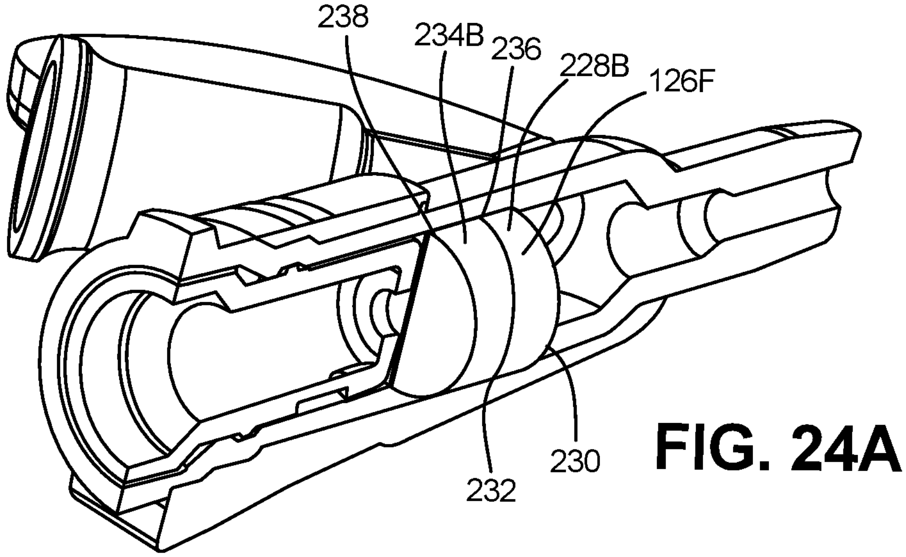
FIG. 24A is a partial cross sectional view depicting a catheter hub, septum retainer and a septum in accordance with an embodiment of the disclosure.
Figure 24B:
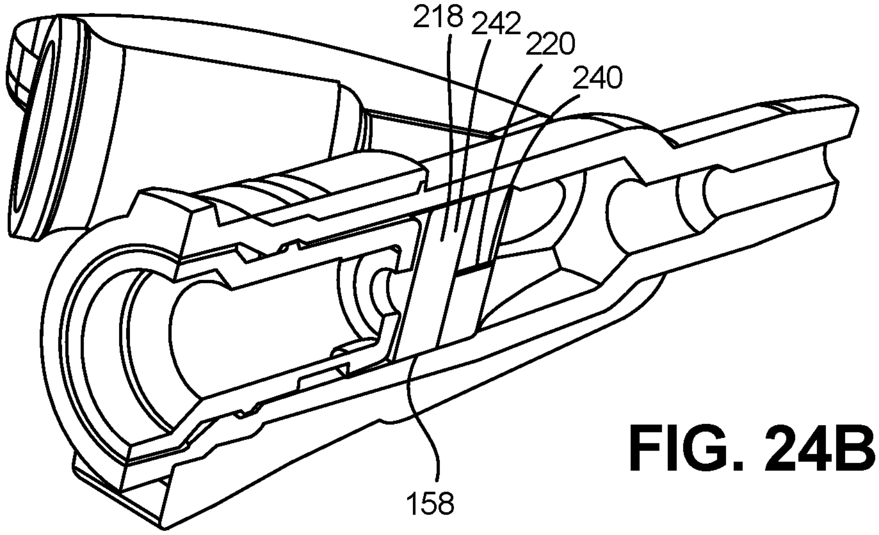
FIG. 24B is a cross sectional view depicting the catheter hub, septum retainer and septum of FIG. 24A.

Referring to FIGS. 22A-B, septum 126D can have an internal surface 216 defining an aperture 220 originating at the distal end 154 and passing through a first thickness 222, and a slit 218 originating at the termination of the aperture 224 and passing through the proximal end 156, thereby passing through a second thickness 226. In one embodiment, the aperture 220 and slit 218 are together configured to enable the needle 104 to pass therethrough. In one embodiment, a portion of slit 218 proximal to aperture 220 can be tapered towards aperture 220. Accordingly, this embodiment complements the reduced drag force of the slit 218 with the good sealing properties of the aperture 220.

Referring to FIGS. 23A-26B, septum 126E-H can include a first septum portion 228A-D having a distal end 230 and a proximal end 232, and a second septum portion 234A-D having a distal end 236 and a proximal end 238, wherein the proximal end 232 of the first septum portion 228A-D is operably coupled to the distal end 236 of the second septum portion 234A-D.

Referring to FIGS. 23A-24B, first septum portion 228A-B can have an internal surface 240 defining an aperture 220 passing from the distal end 230 to the proximal end 232. Second septum portion 234A-B can have an internal surface 242 defining a slit 218 passing from the distal end 236 to the proximal end 238. In some embodiments, the slit 218 can pass entirely through second septum portion 234A-B to the outer perimeter 158. The aperture 220 and slit 218 together are configured to enable an insertion needle to pass therethrough. In other embodiments, the slit 218 can be smaller, such that it does not extend to the outer perimeter 158. For example, the length of the slit can be 0.040 inches, 0.060 inches, or 0.080 inches.

Figure 25A:
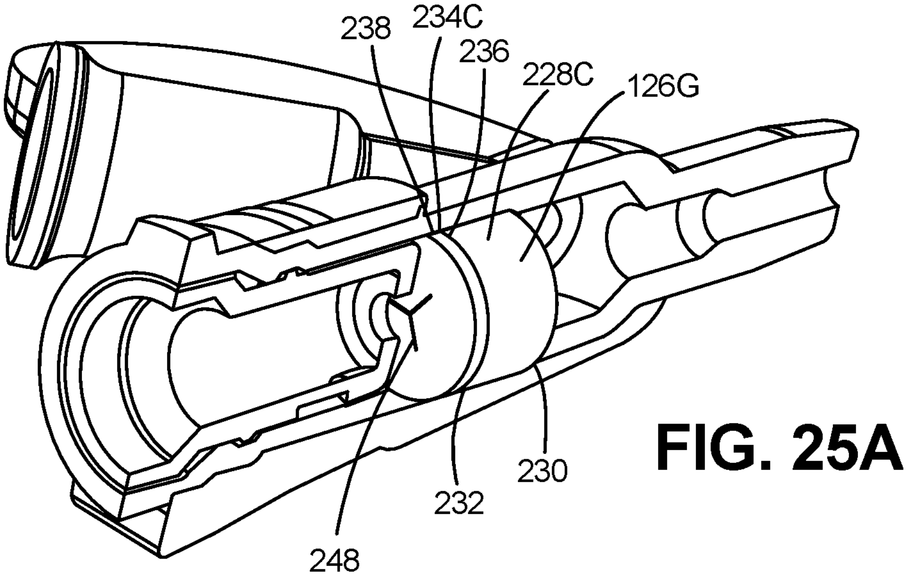
FIG. 25A is a partial cross sectional view depicting a catheter hub, septum retainer and a septum in accordance with an embodiment of the disclosure.
Figure 25B:
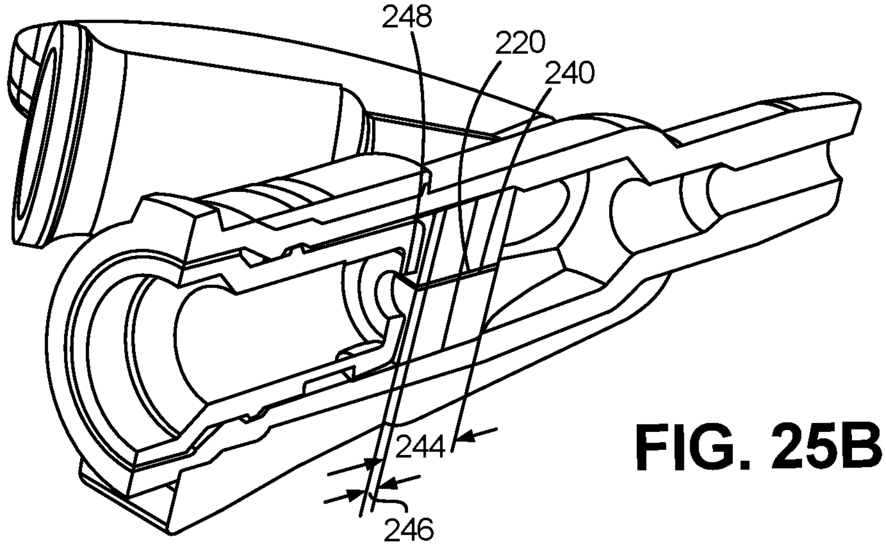
FIG. 25B is a cross sectional view depicting the catheter hub, septum retainer and septum of FIG. 25A.

Referring to FIGS. 25A-B, the thickness 244 of the first septum portion 228C can be greater than the thickness 246 of the second septum portion 234C. In other embodiments, the thickness 244 of the first septum portion 228C can be less than, or substantially equal to the thickness 246 of the second septum portion 234C. In one embodiment, the first septum portion 228C can have an internal surface 240 defining an aperture 220 passing from the distal end 230 to the proximal end 232. Second septum portion 234C can have an internal surface 240 defining a plurality of slits 248 passing from the distal end 236 to the proximal end 238. For example, as depicted, in one embodiment, the plurality of slits 248 can be in a tri-slit configuration. In one embodiment, the aperture 220 and plurality of slits 248 together are configured to enable an insertion needle to pass therethrough. Additionally, in some embodiments, the first septum portion 228 and/or the second septum portion 234 can have a larger diameter than the inside of the catheter hub body 130, such that the septum portion 228, 234 can be circumferentially compressed within the catheter hub body 130.

Figure 26A:
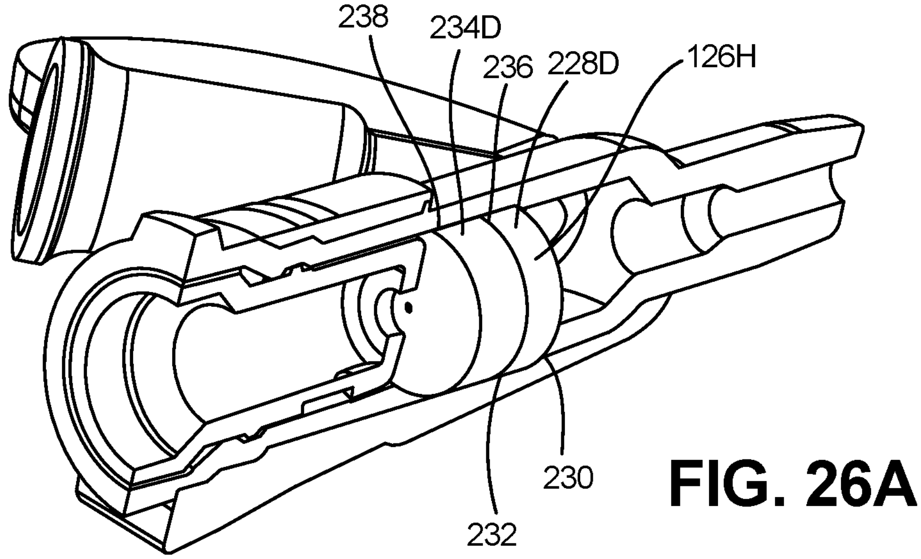
FIG. 26A is a partial cross sectional view depicting a catheter hub, septum retainer and a septum in accordance with an embodiment of the disclosure.
Figure 26B:
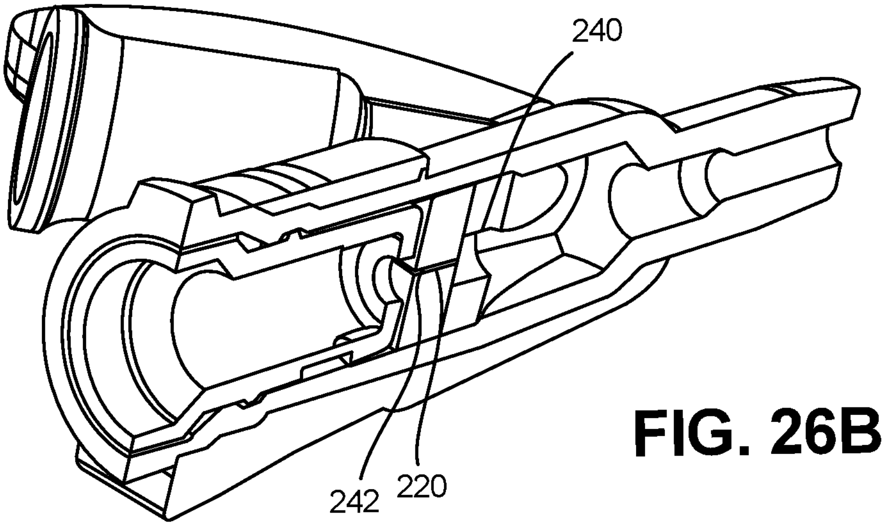
FIG. 26B is a cross sectional view depicting the catheter hub, septum retainer and septum of FIG. 26A.

Referring to FIGS. 26A-B, first septum portion 228D can have an internal surface 240 defining a large diameter aperture 250 passing from the distal end 230 to the proximal end 232. Second septum portion 234D can have an internal surface 242 defining an aperture 220 passing from the distal end 236 to the proximal end 238. In one embodiment, the aperture 220 and aperture 250 together are configured to enable an insertion needle to pass therethrough. In one embodiment, the aperture 250 can be slightly smaller than the diameter of the needle 104 that passes therethrough.

C. Extension Tube and Clamp

Referring to FIGS. 2A-G, an extension tube 114 and an optional extension tube clamp 116 are depicted in accordance with an embodiment of the disclosure. In one embodiment, the extension tube 114 can be substantially transparent or translucent to enable the observation of fluid within the extension tube 114. In one embodiment, the optional extension tube clamp 116 can be constructed of a resilient material that can be deformed to selectively occlude the extension tube 114 to restrict the passage of fluid.

D. Needleless Connector

Figure 27A:
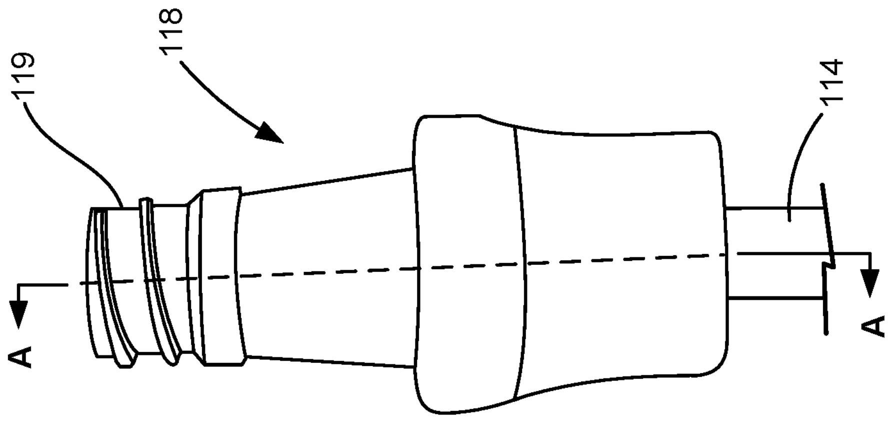
FIG. 27A is a profile view depicting a needleless connector in accordance with an embodiment of the disclosure.
Figure 27B:
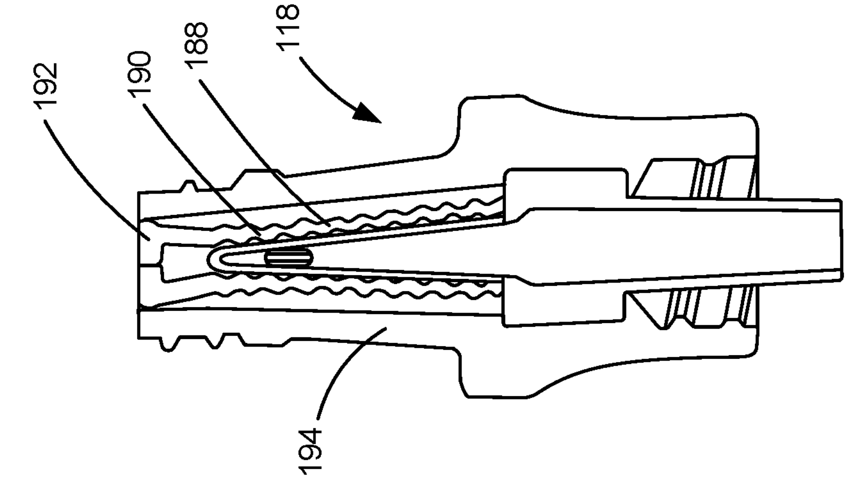
FIG. 27B is a cross sectional view depicting the needleless connector of FIG. 27A in a closed configuration.
Figure 27C:
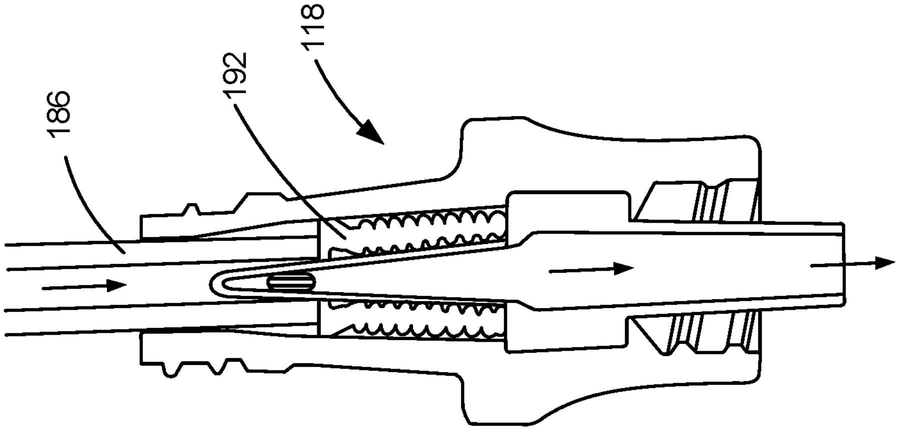
FIG. 27C is a cross sectional view depicting the needleless connector of FIG. 27A in an open configuration coupled to an IV fluid supply.

Referring to FIGS. 27A-C, a needleless connector 118 is depicted in accordance with an embodiment of the disclosure. In one embodiment, the needleless connector 118 is configured to connect the extension tube 114 to a connector of an IV fluid supply line, as partially shown in FIG. 27C. In particular, the needleless connector 118 can be biased to a closed or sealed position (as depicted in FIG. 27B). Connection of the needleless connector 118 to an IV fluid supply 186 can cause the needleless connector 118 to shift to the open position (as depicted in FIG. 27C). Upon disconnection of the needleless connector 118 from the IV fluid supply 186, the needleless connector 118 can be biased back to the closed or sealed position.

In one embodiment, the needleless connector 118 includes a Luer lock connector 119 for connection to an IV fluid supply 186. For example, needleless connector 118 can be a connector described in U.S. Pat. No. 7,713,248 (depicting a needle-free connector marketed by ICU Medical, Inc. under the CLAVE trademark), which is hereby incorporated by reference.

In one embodiment, the needleless connector 118 is comprised of a conical internal conduit 188 with one or more fluid path windows 190, a flexible compression seal 192 capable of selectively covering the internal conduit 188, and a housing 194 substantially surrounding the internal conduit 188 and the compression seal 192. The exterior of housing 194 can have a substantially smooth surface, in which crevices are minimized to promote ease in having a surface that is readily swabbed or cleaned to prevent the growth and/or presence of microbes. The interior of housing 194 can be configured to promote a more even flow of fluid to improve flushability of the needleless connector 118. In one embodiment, the interior of housing 194 can be shaped to reduce the occurrence of dead spaces or pockets, thereby reducing the areas where microbial growth is likely to occur.

Needleless connector 118 can prevent the escape of bodily fluid and/or guard against contamination of the fluid path. As depicted in FIG. 27B, in the closed or sealed position, the compression seal 192 extends over the fluid path windows 190 of internal conduit 188, thereby creating a fluid seal to prevent fluid from escaping from the extension tube 114. Conversely, as depicted in FIG. 27C, when an IV fluid supply connector 186 is inserted into the housing 194, the compression seal 192 is shifted to an open position, thereby exposing the fluid path windows 190 to the fluid path of the IV fluid supply connector 186. Accordingly, the needleless connector 118 selectively enables the flow of fluid through the extension tube 114, while both sealing the intravenous catheter assembly 100 from the ambient environment and inhibiting the escape of bodily fluid from a patient when the IV fluid supply connector 186 is not attached.

Needleless connector 118 thus enables the intravenous catheter assembly 100 to act as a closed system when not connected to either the catheter insertion device 102 or an IV fluid supply connector 186. That is the needleless connector 118, in combination with various embodiments of the vent cap described herein, prevent blood from escaping from the intravenous catheter assembly 100 until an IV fluid supply 186 (or other similar type device) is connected. Additionally, the interior portions of the needleless connector 118 and the extension tube 114 are protected from exposure to the ambient environment. By contrast, many conventional designs (such as that depicted in FIGS. 1A-B) employ only a Luer lock connector 68. Accordingly, prior to connecting the catheter 52 to an IV fluid supply, a clamp 66 designed to crimp the extension tube 64 is engaged to prevent blood from flowing freely from the patient when the needle assembly 50 is removed. Moreover, the interior of the extension tube 64 between the clamp 66 and the Luer lock connector 68 is exposed to the ambient environment prior to connection to an IV fluid supply.

Figure 28:
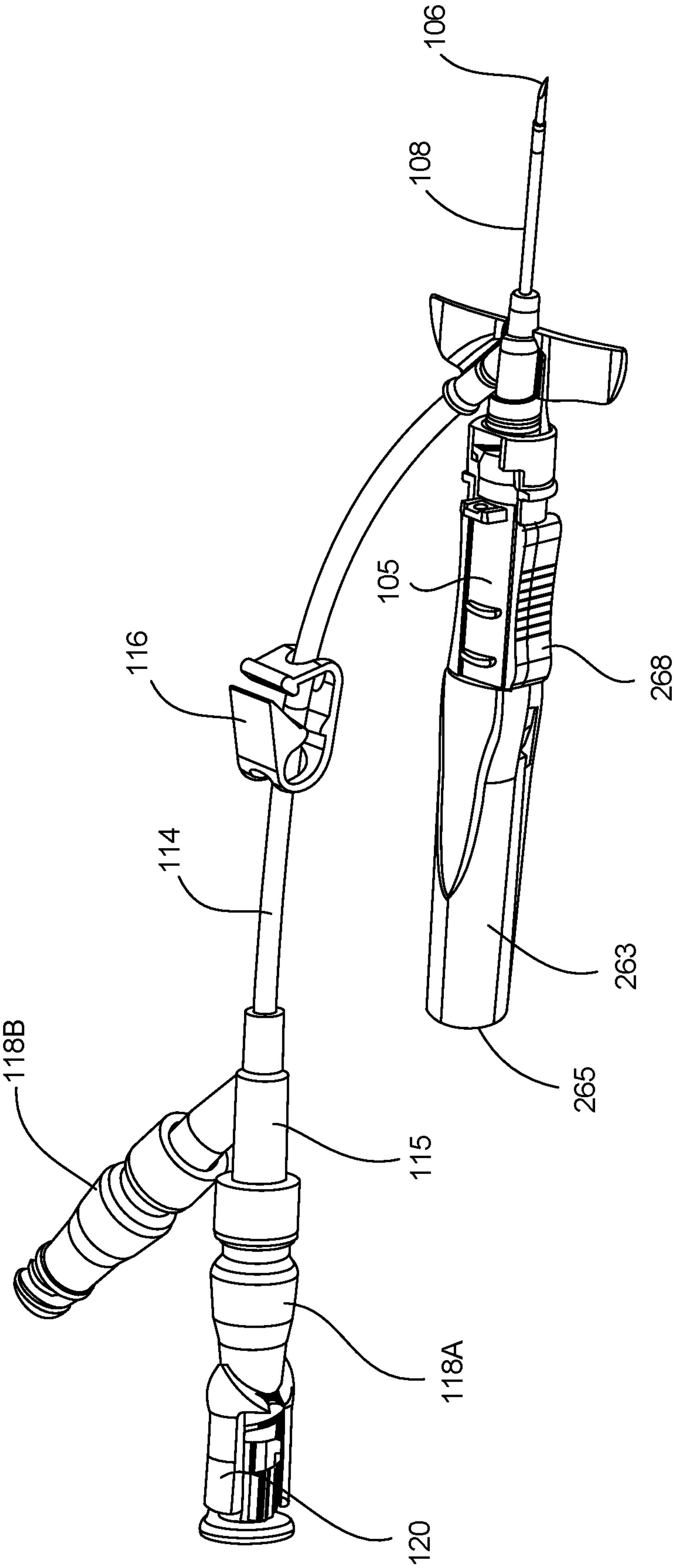
FIG. 28 is a perspective view of an intravenous catheter assembly having a "Y" connector connecting to two needleless connectors in accordance with an embodiment of the disclosure.

Referring to FIG. 28, an intravenous catheter assembly 100 having a first needleless connector 118A and a second needleless connector 118B is depicted in accordance with an embodiment of the disclosure. In other embodiments, the intravenous catheter assembly 100 can include more than two needleless connectors. Needleless connectors 118A/B can be operably coupled to extension tube 114 by a "Y" coupling 115. In one embodiment, coupling 115 is fixedly coupled to the extension tube 114 at one end, and includes one or more portions of a Luer lock connection at the other ends for respective coupling to needleless connectors 118A/B.

E. The Vent Cap

Referring to FIGS. 29A-C, various views of a vent cap 120 are depicted in accordance with n embodiment of the disclosure. One function of the vent cap 120 is to shift the needleless connector 118 from the closed or sealed position to the open position when an IV fluid supply 186 is not attached to the needleless connector 118 for the purpose of venting gas trapped within the intravenous catheter assembly 100 while preventing the escape of blood. In particular, under normal conditions bodily fluid from a patient in which the catheter tube 108 has been inserted can provide the necessary pressure to push the trapped gas through the vent cap 120. In some embodiments, the vent cap 120 can be disposable after use.

Accordingly, during or after the catheter insertion procedure, blood or bodily fluid from a patient enters the catheter tube 108 and other portions of the intravenous catheter assembly 100, thereby purging air from within the catheter assembly 100, either through a gas porous barrier of the catheter insertion device 102 or the needleless connector 118, when activated by the vent cap 120. In some embodiments, the compression seal 192 can be shipped with a vent cap 120 assembled thereto in an activated or open position. However, it has been found that extended compression of the compression seal 192 of some needleless connector 118 embodiments can cause the compression seal 192 to permanently deform. Accordingly, some example embodiments are configured with a vent cap 120 that can be coupled to the needleless connector 118 in a first, initial position, where the vent cap 120 is retained by the needleless connector 118 with the needleless connector 118 in a closed or sealed position. In connection with the catheter insertion procedure, or shortly thereafter, the vent cap 120 can be moved or shifted to a second position to compress the compression seal 192, thereby shifting the needleless connector 118 to the open position and enabling the purging of the air trapped therein.

In one embodiment, the vent cap 120 can include a nose 196, a flash plug 198, a push plate 202, and one or more needleless connector engagement arms 204. Nose 196 can be sized and shaped to fit within the housing 194 of the needleless connector 118 in place of the IV fluid supply connector 186. In some embodiments, the nose 196 can be tapered. Nose 196 can include a vent path wall 206 defining a vent path 208. The vent path 208 can have a diameter sufficient to receive the portion of internal conduit 188 that would otherwise extend into the IV supply connector, such that the fluid path windows 190 of the needleless connector 118 at least partially reside within the vent path 208. A distal end 210 of the nose 196 can be in abutting contact with the compression seal 192 and can provide a fluidic seal therebetween.

Figure 30A:
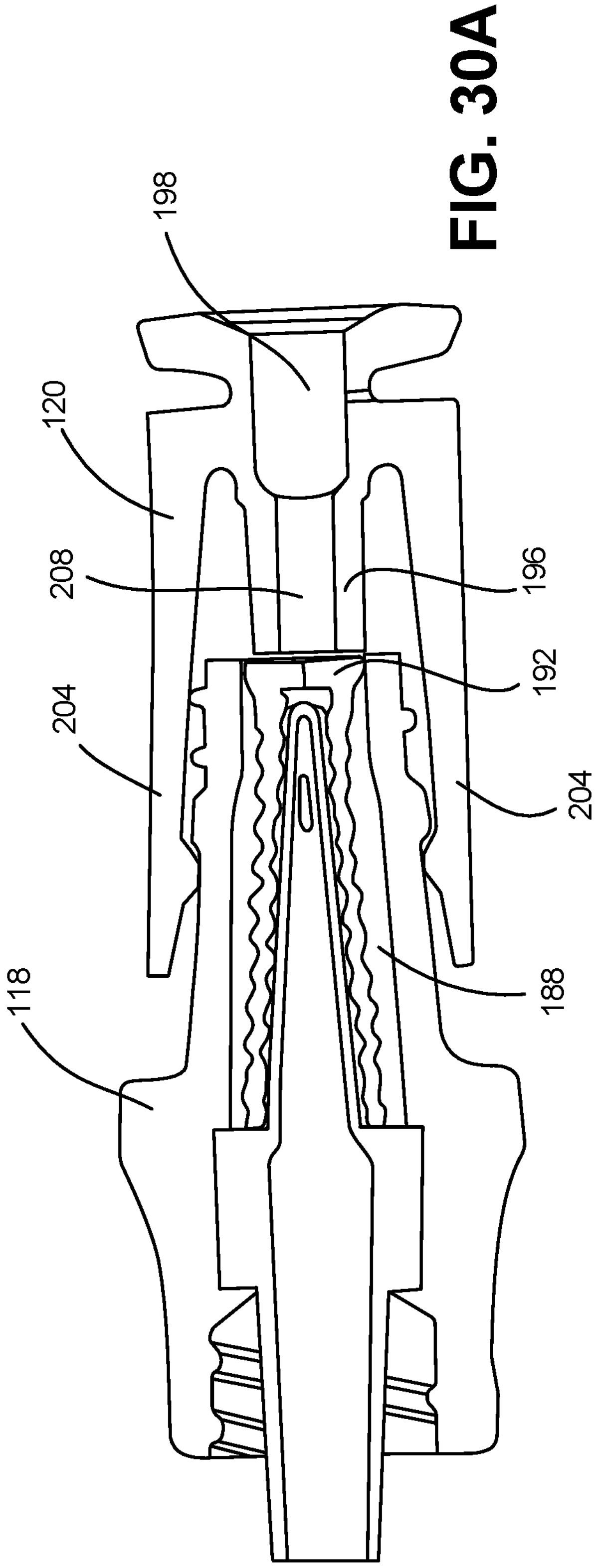
FIG. 30A is a cross-sectional view depicting a vent cap and needleless connector in accordance with an embodiment of the disclosure, wherein the vent cap is in a first, storage position relative to the needleless connector.
Figure 30B:
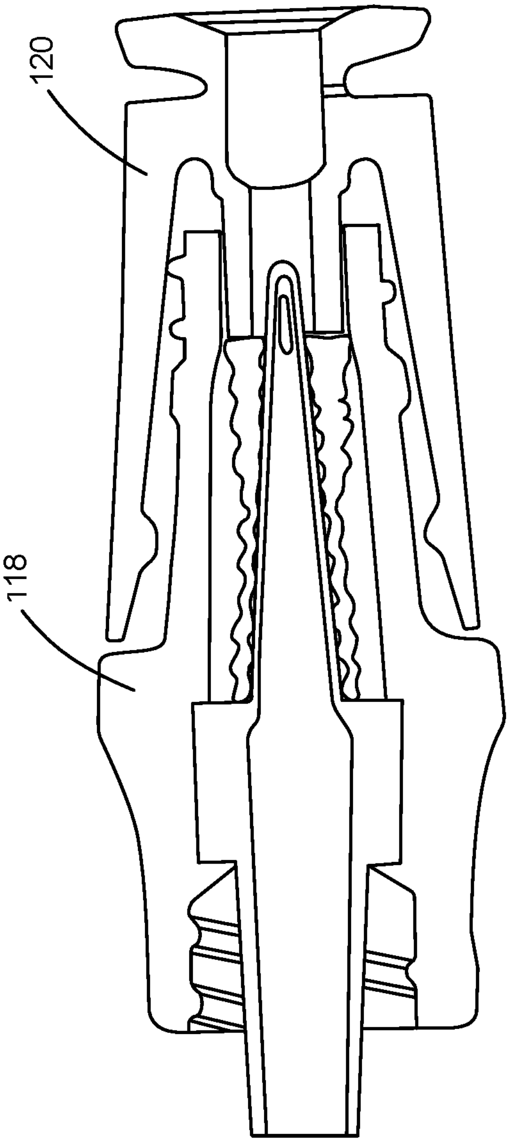
FIG. 30B is a cross-sectional view depicting the vent cap and needleless connector of FIG. 30A, wherein the vent cap is in a second, actively depressed position relative to the needleless connector.

Referring to FIGS. 30A-B, the vent cap 120 can be assembled to a needleless connector and movable or shiftable between a first, storage position (as depicted in FIG. 30A), in which the compression seal 192 of the needleless connector 118 is in an uncompressed state, thereby inhibiting fluid from passing through the vent path 208, and a second, actively depressed position (as depicted in FIG. 30B), in which the compression seal 192 of the needleless connector 118 is in a compressed state, thereby permitting fluid to pass through vent path 208.

Air permeable barrier 198 can be positioned within a portion of the vent path 208. Air permeable barrier 198 can be comprised of an air permeable matrix that enables air or gas to vent as blood or bodily fluid fills the vent path 208, but inhibits the blood or bodily fluid from passing entirely through the vent path 208. In some embodiments, the vent cap 120 can be constructed of a transparent or translucent material. During the venting of air, blood or other bodily fluid can fill a portion of the vent path 208, thereby providing a visual confirmation to the clinician that the catheter tube 108 has been inserted into a patient's vein. Such visual confirmation can be referred to as secondary or tertiary flashback, wherein a primary and/or secondary flashback occurs in one or more flashback indicators associated with the catheter insertion device 102. For example, in one embodiment, upon insertion of the needle 104 into the vein of the patient, a clinician may initially see flashback as blood flow passes through the notch 276 and into the annular space that lies between the exterior of the needle 104 and the interior of the catheter tube 108. A secondary flashback indication may be present when blood from the patient flows proximally through the lumen of the needle 104 and into the flashback chamber 272. A tertiary flashback indication may be present when blood flows through the catheter tube 108, extension tube 114, needleless connector 118, and into vent path 208. The time differential between the initial, secondary and tertiary flashbacks may enable a clinician to confirm that the needle has not extended beyond the subject's vasculature, as may be associated with infiltration/extravasation.

Nose 196 can terminate in a push plate 202. Push plate 202 can include a flange 212 configured to provide a surface area for a clinician to push on as the vent cap 120 is manually shifted between the first, storage position and the second, actively depressed position. In one embodiment, a portion of the vent path wall 206 can further define an eyelet 214. Eyelet 214 can be configured to provide a fluid path for venting air between the vent path 208 and an exterior of the vent path wall 206. In particular, eyelet 214 can provide a path for escaping air in the event that the clinician seals the end of the vent path 208 with their finger as the vent cap 120 is shifted to the second, actively depressed position. In one embodiment, portions of the vent cap 120 can include a mechanism configured to provide an audible click and/or tactile feedback when the vent cap 120 has been shifted to the second, actively depressed position.

The one or more needleless connector engagement arms 204 can be configured to grip a portion of the needleless connector 118. In one embodiment, one or more needleless connector engagement arms 204 can include a ridge 203 to improve a grip of the one or more needleless connector engagement arms to the needleless connector 118. In some embodiments, the needleless connector engagement arms 204 can be constructed of a resilient material, such that the needleless connector engagement arms 204 tend to regain their original shape after temporary deformation. In some embodiments, the resiliency of the needleless connector arms 204 enables the vent cap 122 to be biased to the first, storage position when coupled to the needleless connector 118. In some embodiments, the outer surface of the housing 194 of the needleless connector 118 can be tapered to increase in diameter, such that when the vent cap 120 is shifted to the second, actively depressed position, the needleless connector engagement arms 204 are deflected away from one another. When the clinician releases the vent cap 20, the resiliency of the needleless connector engagement arms 204 can bias the vent cap 120 back to the first, storage position. Accordingly, biasing the vent cap 122 to the first, storage position reduces the likelihood that the compression seal 192 of the needleless connector 118 will permanently deform, as can occur when the compression seal 192 is compressed for long periods of time, according to some embodiments.

F. Operation

In operation, placement of intravenous catheter assembly 100 generally includes preparation of the biological site of the patient. Often a tourniquet is applied proximal to the biological site and a variety of techniques can be used to dilate the patient's vein. While wearing disposable gloves, the clinician cleanses the biological site and a vein is retracted or anchored by placing a thumb over the vein about fifty to seventy-five mm distal to the site.

Figure 31A:
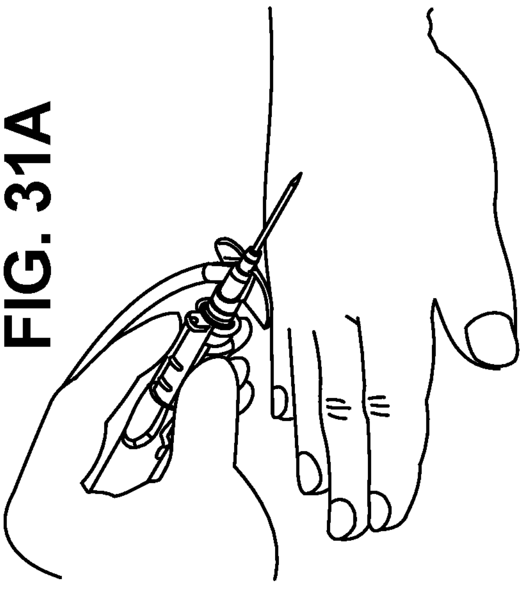
FIG. 31A depicts the preparation of a biological site for insertion of a catheter insertion device in accordance with an embodiment of the disclosure.

Referring to FIG. 31A, the needle 104 and catheter tube 108 are introduced into the vein by inserting the bevel of the sharp needle tip 106 into the vein at about a twenty to thirty degree angle with the bevel facing up in order to pierce one wall of the vein. In some embodiments, during this process the clinician grips the catheter insertion device 102 for optimum control. If successful, blood from the vein flows through the lumen of the needle 104, thereby providing a positive indication of vein entry through one or more flashback mechanisms.

Figure 31B:
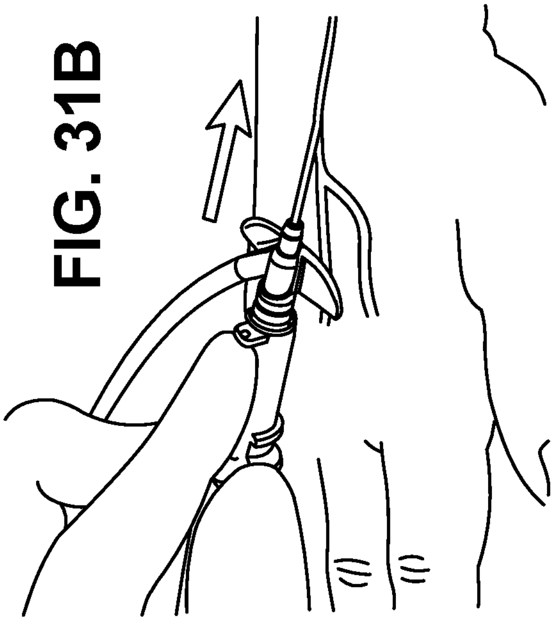
FIG. 31B depicts the insertion of a needle and catheter tube into the vein of a patient in accordance with an embodiment of the disclosure.

Referring to FIG. 31B, to finish placement, the intravenous catheter assembly 100 is lowered towards the skin to decrease the entry angle, and the catheter tube 108 is advanced slightly into the vein. The needle 104 is loosened and the catheter tube 108 is gently advanced farther up into the vein until the catheter hub 110 is against the biological site.

Figure 31C:
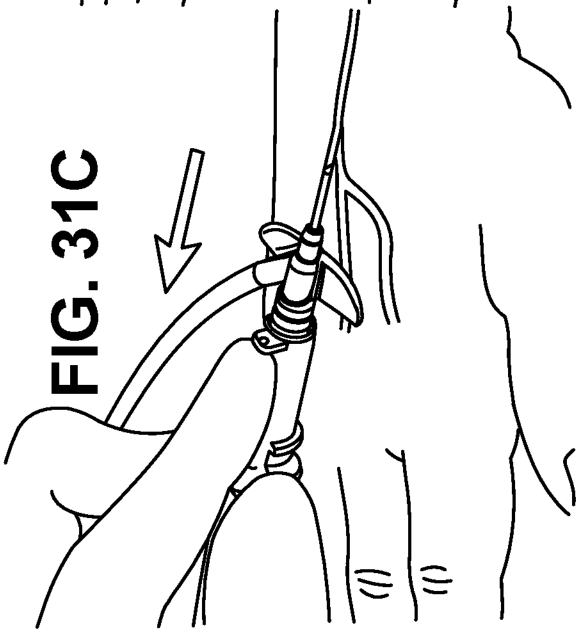
FIG. 31C depicts the retraction of the needle from the catheter tube in accordance with an embodiment of the disclosure.

Referring to FIG. 31C, the tourniquet is loosened and the needle 104 is withdrawn from the catheter tube 108. As the needle 104 is withdrawn, the sharp needle tip 106 is withdrawn through catheter tube lumen 128 and the septum 132. As the sharp needle tip 106 passes through the septum 132, the self-sealing nature of the septum 132 closes any void left by the needle 104 to create a fluid tight barrier. As the needle 104 is further withdrawn, the needle transition 266 shifts the actuator 306 of the passive release mechanism 298 proximally, thereby enabling release of the catheter assembly 100 from the catheter insertion device 102.

The clinician can then secure the catheter assembly 100 in place by securing the catheter hub 110 and/or wing assembly 112 to the biological site by gauze and adhesive tape. The air or gaseous fluid trapped within the catheter assembly 100 can be vented by moving the vent cap 120 from the first, storage position to the second actively depressed position, thereby both evacuating the air within intravenous catheter assembly 100, as well as providing a positive indication of placement of the catheter tube 108 in the patient's vein through a flashback mechanism.

Needleless connector 118 can then be connected to an IV fluid supply 186 configured to supply medicament to a patient, or withdraw fluid from the patient. Extension tube clamp 116 can be manipulated as desired to open and close the fluid path of extension tube 114.

Figure 31D:
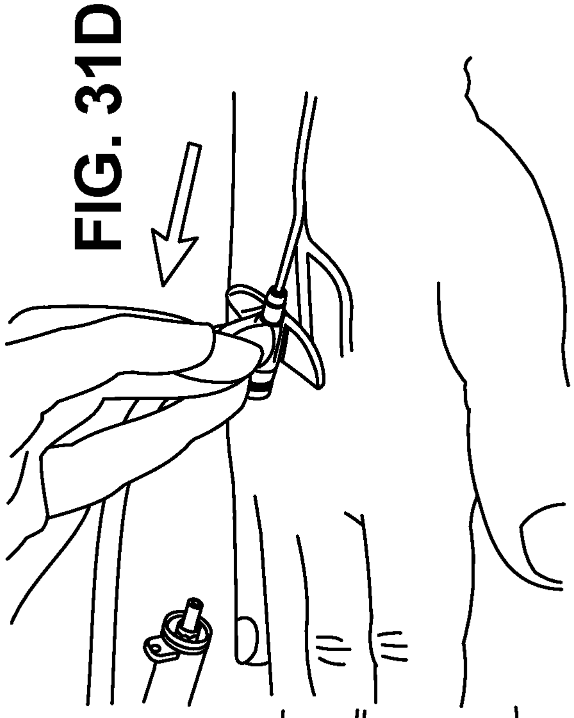
FIG. 31D depicts the removal of a catheter insertion device from a biological site in accordance with an embodiment of the disclosure.

Referring to FIG. 31D, when appropriate to remove the catheter assembly 100, the clinician can remove the gauze and/or adhesive tape securing the catheter hub 110 and/or wing assembly 112 to the biological site of the patient. The catheter assembly 100 can then be gently extracted by pulling on the assembly in the direction indicated by the arrow of FIG. 31D.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

Various example intravenous catheter assembly 100 embodiments are described herein for use in accessing the vein of the subject. It is to be appreciated, however, that the example embodiments described herein can alternatively be used to access the vasculature of a subject in locations other than the vein, including but not limited to the artery of the subject. It is additionally to be appreciated that the term "clinician" refers to any individual that can perform a catheter insertion procedure with any of the example embodiments described herein or combinations thereof. Similarly, the term "subject," as used herein, is to be understood to refer to an individual or object in which a catheter is to be inserted, whether human, animal, or inanimate. Various descriptions are made herein, for the sake of convenience, with respect to procedures being performed by a clinician to access the vein of the subject, while the disclosure is not limited in this respect.

Persons of ordinary skill in the relevant arts will recognize that embodiments may comprise fewer features than illustrated in any individual embodiment described above. The embodiments described herein are not meant to be an exhaustive presentation of the ways in which the various features may be combined. Accordingly, the embodiments are not mutually exclusive combinations of features; rather, embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim.

Moreover, reference in the specification to "one embodiment," "an embodiment," or "some embodiments" means that a particular feature, structure, or characteristic, described in connection with the embodiment, is included in at least one embodiment of the teaching. The appearances of the phrase "in one embodiment" in various places in the specification are not necessarily all referring to the same embodiment.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of Section 112, sixth paragraph of 35 U.S.C. are not to be invoked unless the specific terms "means for" or "step for" are recited in a claim.

The invention claimed is:

1. A vent cap operably coupleable to a needleless connector having a housing with a connector end, the vent cap shiftable relative to the needleless connector between a storage position and a venting position, the vent cap comprising:

a nose defined by a wall between a distal end and a proximal end, the distal end proximal to the connector end of the needleless connector when the vent cap is coupled to the needleless connector in the storage position, the nose adapted to be inserted at least partially into the housing of the needleless connector when the vent cap is in the venting position;

a push plate having a flange configured to provide a surface area for a clinician to push on includes an opening operably coupled to the proximal end of the nose; and one or more resilient needleless connector engagement arms operably coupled to the nose and configured to grip a portion of the housing of the needleless connector to enable the vent cap to move from the storage position to the venting position when the plate is being actively depressed.

2. The vent cap of claim 1, wherein the distal end of the nose is in abutment contact with a free end of a flexible compressible seal selectively covering an internal conduit in the housing of the needleless connector in the storage position.

3. The vent cap of claim 2, wherein when the vent cap is in the venting position, the flexible compressible seal is compressed by the distal end of the nose to expose the internal conduit so as to permit air to pass from the internal conduit to a vent path of the vent cap.

4. The vent cap of claim 1, wherein the vent cap is shiftable from the storage position to the venting position when the push plate is actively depressed in the distal direction relative to the needleless connector such that the nose of the vent cap is inserted at least partially into the housing of the needleless connector to enable air trapped within the needleless connector to be purged from the vent cap.

5. The vent cap of claim 1, wherein when the push plate is actively depressed in the distal direction relative to the needleless connector to shift the vent cap to the venting position, the one or more resilient needleless connector engagement arms are forced apart by a tapered portion of the housing with increasing diameter toward the connector end of the needleless connector; and wherein the vent cap is biased back to the storage position by the one or more resilient needleless connector engagement arms returning to their original shape when the push plate is no longer being actively depressed in the distal direction.

6. The vent cap of claim 1, wherein the vent cap is removable from the needleless connector after use.

7. The vent cap of claim 1, wherein the wall of the nose defines a vent path between the distal end and the proximal end, an air permeable barrier positioned in the vent path to enable air in the vent path to vent out through the opening of the push plate.

8. The vent cap of claim 7, wherein the wall defining the vent path is constructed of at least one of a transparent and translucent material to provide a flashback indication as fluid flows into the vent path.

9. The vent cap of claim 1, wherein the wall of the nose defines a vent path that extends from the distal end to the opening at the push plate, an eyelet through the wall distal of the push plate provides a fluid path to enable air to escape from the vent path when the opening at the push plate is blocked.

10. The vent cap of claim 1, wherein the one or more resilient needleless connector engagement arms include a ridge to improve the grip of the one or more resilient needleless connector engagement arms to the housing of the needleless connector.

11. The vent cap of claim 1, wherein the nose of the vent cap is tapered to improve a fluid tight seal with the needleless connector when the vent cap is shifted between the storage position and the venting position.

12. A closed system catheter assembly, comprising:

a catheter hub having a distal end and an open proximal end, an internal passage defined by a wall extending between the distal and proximal ends, a catheter extending distally from the distal end, a side port to the internal passage, and an extension tube connected to the side port to establish a fluid path between the internal passage and the extension tube;

a needleless connector having a housing including one end connected to the extension tube and a connector end; and a vent cap adapted to operably couple to the needleless connector, the vent cap shiftable relative to the needleless connector between a storage position and a venting position, the vent cap including a nose defined by a wall between a distal end and a proximal end, the distal end proximal to the connector end of the needleless connector when the vent cap is coupled to the needleless connector in the storage position, the nose adapted to be inserted at least partially into the housing of the needleless connector when the vent cap is in the venting position;

a push plate having a flange configured to provide a surface area for a clinician to push on includes an opening operably coupled to the proximal end of the nose; and one or more resilient needleless connector engagement arms operably coupled to the nose and configured to grip a portion of the housing of the needleless connector to enable the vent cap to move from the storage position to the venting position when the plate is being actively depressed.

13. The closed system catheter assembly of claim 12, wherein the distal end of the nose is in abutment contact with a free end of a flexible compressible seal selectively covering an internal conduit in the housing of the needleless connector in the storage position; and wherein when the vent cap is in the venting position, the flexible compressible seal is compressed by the distal end of the nose to expose the internal conduit so as to permit fluid to pass from the internal conduit to a vent path of the vent cap.

14. The closed system catheter assembly of claim 12, wherein the vent cap is shiftable from the storage position to the venting position when the push plate is actively depressed in the distal direction relative to the needleless connector such that the nose is inserted at least partially into the housing of the needleless connector to enable air trapped within the needleless connector to be purged from the vent cap.

15. The closed system catheter assembly of claim 12, wherein the vent cap is shifted to the venting position and the one or more resilient needleless connector engagement arms are forced apart by being in contact with a tapered portion of the housing with increasing diameter toward the one end of the needleless connector when the push plate is being actively depressed in the distal direction relative to the needleless connector; and wherein the vent cap is biased back to the storage position by the one or more resilient needleless connector engagement arms returning to their original shape when the push plate is no longer being actively depressed.

16. The closed system catheter assembly of claim 12, wherein the wall of the nose defines a vent path between the distal end and the proximal end, an air permeable barrier positioned in the vent path to enable air in the vent path to vent out through the opening of the push plate.

17. The closed system catheter assembly of claim 12, further comprising:

an eyelet through the wall distal of the push plate providing a fluid path to enable air to escape from the vent path when the opening at the push plate is blocked.

18. The closed system catheter assembly of claim 12, wherein the wall is constructed of at least one of a transparent and translucent material to provide a flashback indication as fluid flows into the vent path.

19. The closed system catheter assembly of claim 12, wherein the vent cap is removable from the needleless connector after use.

* * * * *